United States Patent
Neelon et al.

(10) Patent No.: US 10,016,449 B2
(45) Date of Patent: Jul. 10, 2018

(54) PHARMACEUTICAL COMPOSITIONS

(71) Applicant: MOMENTA PHARMACEUTICALS, INC., Cambridge, MA (US)

(72) Inventors: Kelly Neelon, Newburyport, MA (US); Gary Mills, Groveland, MA (US); James Anderson, Hudson, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 133 days.

(21) Appl. No.: 14/893,516

(22) PCT Filed: May 27, 2014

(86) PCT No.: PCT/US2014/039542
§ 371 (c)(1),
(2) Date: Nov. 23, 2015

(87) PCT Pub. No.: WO2014/193818
PCT Pub. Date: Dec. 4, 2014

(65) Prior Publication Data
US 2016/0129028 A1    May 12, 2016

Related U.S. Application Data

(60) Provisional application No. 61/828,116, filed on May 28, 2013.

(51) Int. Cl.
*A61K 31/7016* (2006.01)
*A61K 9/00* (2006.01)
*A61K 47/12* (2006.01)
*A61K 47/18* (2017.01)

(52) U.S. Cl.
CPC ........ *A61K 31/7016* (2013.01); *A61K 9/0019* (2013.01); *A61K 47/12* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 3,118,816 A | 1/1964 | Gushing et al. | |
| 4,235,871 A | 11/1980 | Papahadjopoulos et al. | |
| 4,303,651 A | 12/1981 | Lindahl et al. | |
| 4,629,699 A | 12/1986 | Bianchini | |
| 4,717,719 A | 1/1988 | Sportoletti et al. | |
| 4,727,063 A | 2/1988 | Naggi et al. | |
| 4,847,338 A | 7/1989 | Linhardt et al. | |
| 4,868,103 A | 9/1989 | Stavrianopoulos et al. | |
| 4,916,219 A | 4/1990 | Linhardt et al. | |
| 4,990,502 A | 2/1991 | Lormeau et al. | |
| 5,262,403 A | 11/1993 | Nicolson et al. | |
| 5,264,425 A | 11/1993 | Dal Pozzo et al. | |
| 5,296,471 A | 3/1994 | Holme et al. | |
| 5,403,827 A | 4/1995 | De-Ambrosi | |
| 5,541,166 A | 7/1996 | Parish et al. | |
| 5,583,121 A | 12/1996 | Chaudry et al. | |
| 5,668,116 A | 9/1997 | Cullis-Hill et al. | |
| 5,668,118 A | 9/1997 | Kennedy | |
| 5,690,910 A | 11/1997 | Ahmed et al. | |
| 5,696,100 A | 12/1997 | Holme et al. | |
| 5,707,974 A | 1/1998 | Kennedy | |
| 5,733,893 A | 3/1998 | Ornitz | |
| 5,763,421 A | 6/1998 | Caretto et al. | |
| 5,767,269 A | 6/1998 | Hirsh et al. | |
| 5,795,875 A | 8/1998 | Holme et al. | |
| 5,808,021 A | 9/1998 | Holme et al. | |
| 5,912,237 A | 6/1999 | Kennedy | |
| 5,990,097 A | 11/1999 | Kennedy | |
| 6,001,820 A | 12/1999 | Hirsh et al. | |
| 6,077,683 A | 6/2000 | Kennedy | |
| 6,127,347 A | 10/2000 | Chaudry et al. | |
| 6,130,210 A | 10/2000 | Caretto et al. | |
| 6,150,342 A | 11/2000 | Mattsson et al. | |
| 6,545,136 B1 | 4/2003 | Hara et al. | |
| 6,596,705 B1 | 7/2003 | Varki et al. | |
| 7,781,416 B2 | 8/2010 | Casu et al. | |
| 7,790,700 B2 | 9/2010 | Casu et al. | |
| 8,067,555 B2 | 11/2011 | Casu et al. | |
| 8,071,569 B2 | 12/2011 | Mousa | |
| 8,569,262 B2 | 10/2013 | Sundaram et al. | |
| 8,592,393 B2 | 11/2013 | Sundaram et al. | |
| 2003/0013682 A1 | 1/2003 | Banito et al. | |
| 2003/0147848 A1 | 8/2003 | Geng | |

(Continued)

FOREIGN PATENT DOCUMENTS

BE   620906   11/1962
CN   1060599 A   4/1992

(Continued)

OTHER PUBLICATIONS

Johnson et al., "Can Cancer Tumors Be Starved to Death"? Retrieved Sep. 20, 2012 (online) <http://www.mhhe.com/biosci/genbio/tlw3/virtual_labs/lab6/labs/resources/original.pdf>.

Kennett, E.G., Davies, M.J. (2009) Glycosaminoglycans are fragmented by hydroxyl, carbonate, and nitrogen dioxide radicals in a site selective manner: implications for peroxynitrite-mediated damage at sites of inflammation. Free Radical Biology & Medicine, vol. 47, p. 389-400.

Koliopanos, A., Friess, H., Kleef, J., Shi, X., Liao, Q., Peeker, I., Vlodaysky, I., Zimmermann, A., Buchler, M.W. (2001) Heparanase Expression in Primary and Metastatic Pancreatic Cancer. Cancer Research, vol. 61, p. 4655-4659.

(Continued)

*Primary Examiner* — Shaojia A Jiang
*Assistant Examiner* — Dale R Miller
(74) *Attorney, Agent, or Firm* — Brenda Herschbach Jarrell; Rolando Medina; Nishat A. Shaikh

(57) ABSTRACT

Described herein are pharmaceutical compositions comprising a LMWH preparation having at least one chain having a glycol split uronic acid residue (UG) in the preparation and uses thereof.

27 Claims, No Drawings

(56) References Cited

U.S. PATENT DOCUMENTS

| | | | |
|---|---|---|---|
| 2004/0056249 | A1 | 3/2004 | Russell et al. |
| 2004/0087544 | A1 | 5/2004 | Russo et al. |
| 2005/0107331 | A1 | 5/2005 | Banito et al. |
| 2005/0137167 | A1 | 6/2005 | Casu et al. |
| 2005/0222084 | A1 | 10/2005 | Casu et al. |
| 2005/0282775 | A1 | 12/2005 | Kennedy |
| 2006/0040896 | A1 | 2/2006 | Kennedy |
| 2006/0172968 | A1 | 8/2006 | Casu et al. |
| 2007/0037814 | A1 | 2/2007 | Rawson et al. |
| 2007/0142323 | A1 | 6/2007 | Viskov et al. |
| 2007/0287683 | A1 | 12/2007 | Shriver et al. |
| 2008/0051567 | A1 | 2/2008 | Casu et al. |
| 2008/0280819 | A1 | 11/2008 | Mulugeta et al. |
| 2009/0012165 | A1 | 1/2009 | Veno |
| 2009/0149424 | A1 | 6/2009 | Byun et al. |
| 2010/0021416 | A1 | 1/2010 | Lichter et al. |
| 2010/0081629 | A1 | 4/2010 | Viskov et al. |
| 2010/0247526 | A1* | 9/2010 | Spee .................. C07K 16/2851 424/133.1 |
| 2010/0316640 | A1 | 12/2010 | Sundaram et al. |
| 2010/0331746 | A1 | 12/2010 | Deslandes |
| 2011/0076729 | A1 | 3/2011 | Mamuwala et al. |
| 2011/0207919 | A1 | 8/2011 | Beccati et al. |
| 2011/0288046 | A1 | 11/2011 | Venkataraman et al. |

FOREIGN PATENT DOCUMENTS

| | | | |
|---|---|---|---|
| EP | 0121067 | A1 | 10/1984 |
| EP | 0140781 | A2 | 5/1985 |
| EP | 0346810 | A2 | 12/1989 |
| EP | 0557887 | A2 | 9/1993 |
| EP | 0735050 | B1 | 10/1996 |
| EP | 1129718 | A2 | 9/2001 |
| EP | 1268558 | A1 | 1/2003 |
| JP | 60115525 | | 6/1985 |
| JP | 2002-501613 | A | 1/2002 |
| JP | 2006501815 | A | 1/2006 |
| JP | 2007-517771 | A | 7/2007 |
| JP | 2008150441 | A | 7/2008 |
| JP | 2009538386 | A | 11/2009 |
| JP | 2010532314 | A | 10/2010 |
| WO | 9012561 | A1 | 11/1990 |
| WO | 199201003 | A1 | 1/1992 |
| WO | 199202232 | A1 | 2/1992 |
| WO | 199217187 | A1 | 10/1992 |
| WO | 199217188 | A1 | 10/1992 |
| WO | 199218545 | A1 | 10/1992 |
| WO | 199629973 | A2 | 10/1996 |
| WO | 9842865 | A1 | 10/1998 |
| WO | 200155221 | A1 | 8/2001 |
| WO | 2002083086 | A1 | 10/2002 |
| WO | 2003022291 | A1 | 3/2003 |
| WO | 200701409 | A2 | 1/2007 |
| WO | 2007014049 | A2 | 2/2007 |
| WO | 2007056218 | A2 | 5/2007 |
| WO | 2007059313 | A1 | 5/2007 |
| WO | 2007144144 | A1 | 12/2007 |
| WO | 2009007224 | A1 | 1/2009 |
| WO | 2009059283 | A1 | 5/2009 |
| WO | 2011130572 | A1 | 10/2011 |
| WO | WO-2011/159770 | A2 | 12/2011 |
| WO | WO-2014/193818 | A1 | 12/2014 |

OTHER PUBLICATIONS

Kondo et al., "Favorable Prognosis of Renal Cell Carcinoma with Increased Expression of Chemokines Associated with a Th1-type Immune Response," Cancer Science, 2006, vol. 97, Iss. 8, pp. 780-786.

Kragh et al., "Non-anti-coagulant heparin inhibits metastasis but not primary tumor growth", Oncology Reports, vol. 14, pp. 99-104 (2005).

Kragh, et al., "Non-anti-coagulant heparins: A promising approach for prevention of tumor metastasis (Review)" International Journal of Oncology, 27:1159-1167 (2005).

Lifespan, "Low Molecular Weight Heparin (LMWH) ELISA Kit for Buffer/Urine Samples" Mar. 8, 2013.

Linhardt, R.J., Gunay, N.S. (1999) Production and Chemical Processing of Low Molecular Weight Heparins. Seminars in Thrombosis and Hemostasis, vol. 25, suppl. 3, p. 5-16.

Lolkema, et al., "Abstract LB-43:M402, a novel heparin sulphate mimetic, synergizes with gemcitabine to improve survival and reduce metastasis and epithelial-to-mesenchymal transition (EMT) in a genetically engineered mouse model for pancreatic cancer" Cancer Research, 70(8 Suppl): Abstract LB-43 (2010).

Mao et al., "Capillary electrophoresis for the analysis fo glycosaminioglycans and glycosaminoglycan-derived oligosaccharides" Biomedical Chromatography, vol. 16, pp. 77-94 (2002).

Mascellani et al., "Structure and Contribution to the heparin cofactor II-mediated inhibition of thrombin of naturally oversulphated sequences of dermatan sulphate" Biochem. J. vol. 296 pp. 639-648 (1993).

Matsumoto et al., "Granulocyte-colony Stimulating Factor-producing Esophageal Carcinoma: Serum Level as a Marker for Monitoring the Effects of Treatment," International Journal of Clinical Oncology, 2000, vol. 5, Iss. 5, pp. 328-333.

Mousa Shaker A: "Role of current and emerging antithrombotics in thrombosis and cancer" Drugs of Today, vol. 42, No. 5, pp. 331-350 (2006).

Naggi et al., "Modulation of the Heparanase-inhibiting Activity of Heparin through Selective Desulfation, Graded N-Acetylation, and Glycol Splitting", The Journal of Biological Chemistry, vol. 280, No. 13, pp. 12103-12113 (2005).

Natori, et al., "G-CSF stimulates angiogenesis and promotes tumor growth: potential contribution of bone marrow-derived endothelial progenitor cells" Biochemical and Biophysical Research Communications, 297:1058-1061 (2002).

Ostrand-Rosenberg Suzanne et al: "Myeloid-Derived Suppressor Cells: Linking Inflammation and Cancer" Journal of Immunology, vol. 182, No. 8, pp. 4499-4506 (2009).

Peters et al., "Randomized comparison of a novel anticoagulant, vasoflux, and heparin as adjunctive therapy to streptokinase for acute myocardial infarction(vasoflux international trial for acute myocardial infarction lysis)", American Heart Journal., vol. 142 (2), pp. 237-243 (2001).

Pisano et al., "Undersulfated, low-molecular-weight glycol-split heparin as an antiangiogenic VEGFantagonist" Glycobiology, vol. 15, No. 2, pp. 1C-6C. (2005).

Riedel et al., "Serum Levels of Matrix Metalloproteinase-2 and -9 in Patients with Head and Neck Squamous Cell Carcinoma," Anticancer Research, 2000, vol. 20, pp. 3045-3050.

Ritchie et al., "A chemically modified heparin, inhibits myeloma growth and angiogenisis via disruption of the heparanase/ syndecan-1 axis", Clin Can Res, pp. 1382-1393 (2011).

Safran, H., Dipetrillo, T., Iannitti, D., Quirk, D., Akerman, P., Gruff, D., Cioffi, W., Shah, S., Ramdin, N., Rich, T. (2002) International Journal of Radiation Oncology Biology Physics, vol. 54, No. 1, p. 137-141.

Sakuma et al., "Particulate Phase of Cellulose Cigarrette Smoke" Agric. Biol. Chem., 44(3):555-561 (1980).

Sasisekharan et al., "Roles of Heparin-Sulphate Glycosaminoglycans in Cancer", Nature Reviews, vol. 2, pp. 521-528 (2002).

Spickler et al., "Clinical evaluation of the pharmacology, and safety of vasoflux[trademark symbol], a novel antithrombotic", Abstracts from the 70th scientific sessions, Nov. 9-12, 1997.

Wang et al., "Enoxaparin-induced alopecia in patients with cerebral venous thrombosis", Journal of Clinical Pharmacy and Therapeutics, vol. 31, No. 5, pp. 513-517 (2006).

Washimi et al., "Measurement of plasma matrix methalloproteinase-9 in diagnosing metastatic bone tumors and evaluating the therapeutic effect," 62nd Proceedings of the Japanese Cancer Association, 2003, p. 48, 3445-PA.

Weitz et al., "Vasoflux, a new anticoagulant with a novel mechanism of action", circ.ahajournals.org, pp. 682-689 (1999).

Written Opinion of the International Seaching Authority for PCT/ US2011/32851 dated Jul. 5, 2011.

(56) References Cited

OTHER PUBLICATIONS

Written Opinion of the International Seraching Authority for PCT/US2008/082223.
Yamada et al., "Isolation of hte Porcine Heparin Testrasaccharides with Glucuronate 2-O-Sulfate" The Journal of Biological Cheminstry, vol. 270, No. 15, pp. 8696-8705 (1995).
Yamashita, et al., "Immunoreactive Hepatocyte Growth Factor Is a Strong and Independent Predictor of Recurrence and Survival in Human Breast Cancer" Cancer Research, 54:1630-1633 (1994).
Yang et al., "Targeting heparanase as a therapy for multiplemyeloma", Abstract # 257, Apr. 18, 2009.
Yao, et al., "Multiple signaling pathways involved in activation of matrix metalloproteinase-9 (MMP-9) by heregulin-beta1 in human breast cancer cells" Oncogene, 20:8066-8074 (2001).
Zea, et al., "Arginase-Producing Myeloid Suppressor Cells in Renal Cell Carcinoma Patients: A Mechanism of Tumor Evasion" Cancer Res., 65(8):3044-3048 (2005).
Zhou, et al., "Abstract #281: M-ONC 402-a non anticoagulant low molecular weight heparin inhibits tumor metastasis" Cancer Research, 69:Abstract 281 (2009).
Alekseeva, A. et al., Profiling glycol-split heparins by high-performance liquid chromatography/mass spectrometry analysis of their heparinase-generated oligosaccharides, Analytical Biochemistry, 434(1):112-122 (2013).
"Fragmin" by RxList: The Internet Drug Index. Retrieved on [Aug. 19, 2014] [online]. Retrieved from the internet at <http://www.rxlist.com/fragmin-drug.htm>.
"Metastasis" Encyclopedia Britannica. Encyclopedia Britannica Online Academic Edition. Encyclopedia Britannica Inc. , 2011. web: Dec. 6, 2011 <http://britannica.com//EBchecked/topic/378021/metastasis>.
Addison, et al., "The CXC Chemokine, Monokine Induced by Interferon-gamma, Inhibits Non-Small Cell Lung Carcinoma Tumor Growth and Metastasis" Human Gene Therapy, 11:247-261 (2000).
Ansel, H.C., Allen, Jr., L.V., Popovich, N.G. (1999) Pharmaceutical Dosage Forms and Drug Delivery Systems, published by Lippincott Williams & Wilkins, p. 48-53 and 120-128.
Apsner et al., "Dalteparin-induced alopecia in hemodialysis patients: reversal by regional cirate anticoagulate as an example" Blood, vol. 97(9) pp. 2914-2915 (2001).
Avci et al., "Synthetic Oligosaccharides as Heparin-Mimetics Displaying Anticoagulant Properties" Current Pharm. Design, 9:2323-2335 (2003).
Bassas P et al., "Anticoagulation and Antiplatelet Therapy in Dermatology", Actas Dermosifiliograficas, vol. 100, No. 1, pp. 7-16 (2009).
Beccati et al., "Identification of a novel structure in heparin generated by potassium permanganate oxidation" Carbohydrate Polymers, 82:699-705 (2010).
Beyer, et al., "Composition of OSCS-contaminated heparin occurring in 2008 in batches on the German market" European Journal of Pharmaceutical Sciences, 40:297-304 (2010).
Casu et al., "Chemical Derivatization as a Strategy to Study Structure-Activity Relationships of Glycosaminoglycans", Seminars in Thrombosis and Hemostasis, col. 28, No. 4, pp. 335-342 (2002).
Casu et al., "Non-Anticoagulant Heparins and Inhibition of Cancer", Pathophysiol Haemost Thromb., vol. 36, pp. 195-203 (2007).
Casu et al., "Retention of Antilipemic Activity by Periodate-oxidized Non-anticoagulant Heparins", Arseneimillel Forschung/Drug Res. vol. 36 (1), No. 4, pp. 637-642 (1986).
Casu et al., "Short Heparin Sequences Spaced by Glycol-Split Uronate Residues Are Antagonists of Fibroblast Growth Factor 2 and Angiogenesis Inhibitors", Biochemistry, vol. 41, pp. 10519-10528 (2002).
Casu et al., "Undersulfated and Glycol-Split Heparins Endowed with Antiangiogenic Activity", J. Med. Chem., vol. 47, pp. 838-848 (2004).
Chinese Search Report from Chinese Application No. 201180019382.7 dated Jun. 7, 2014.

Chu et al., "Abstract #5005: M-ONC 402, a novel low molecular weight heparin (LMWH), interacts with heparin-binding proteins and inhibits metastic seeding of tumor cells in mice" Cancer Research, 69:Abstract 5005 (2009).
Cui et al., "Structure Analysis of Polysaccharides" Food Carbohydrates: Chemistry, Physical Properties and Applications (2005).
De Lorenzo Ferruccio et al: "The role of anticoagulation in cancer patients: Facts and figures" Anti-Cancer Agents in Medicinal Chemistry, vol. 6, No. 6, pp. 579-587 (2006).
Definition of "prevention" from the Institute for International Medical Education [online], [retrieved on Mar. 24, 2011]. retrieved from the internet <http://www.iime.org/glossary.htm>. Published Feb. 2002. p. 1, 2, 26, 27 and 39.
Derbyshire et al., "Anti-tumor and Anti-angiogenic effects in Mice of Heparin Conjugated to Angiostatic Steriods" Int. J. Cancer vol. 63 pp. 694-701 (1995).
Diaz-Montero et al., "Increased circulating myeloid-derived suppressor cells correlate with clinical cancer stage, mestastatic tumor burden, and doxorubicin-cyclophosphamide chemotherapy", Cancer Immunology Immunotherapy, vol. 58, No. 1 pp. 49-59 (2009).
Extended European Search Report from European Application No. 11769624.5 dated Jun. 26, 2013.
Extended European Search Report from European Application No. 11769718.5 dated Jul. 12, 2013.
Ferro Vito et al: "PI-88 and novel heparan sulfate mimetics inhibit angiogenesis" Seminars in Thrombosis and Hemostasis, vol. 33, No. 5, pp. 557-562 (2007).
Fransson et al., "Relationship between anticoagulant activity of heparin and susceptibility to periodate oxidation", Department of Physiological Chemsitry, vol. 97, No. 1, pp. 119-123 (1979).
Gabrilovich Dmitry I et al: "Myeloid-derived suppressor cells as regulators of the immune system" Nature Reviews Immunology, vol. 9, No. 3, pp. 162-174 (2009).
Gerotziafas et al., "Effect of the anti-factor Xa and anti-factor IIa activities of low-molecular-weight heparins upon the phases of thrombin generation" Journal of Thrombosis and Haemostasis, 5:955-962 (2007).
Gerotziafas G T et al: "Clinical studies with anticoagulants to improve survival in cancer patients" Pathophysiology of Haemostasis and Thrombosis 2008 S. Karger AG CHE LNKD—DOI:10.1159/000175158, vol. 36, No. 3-4, pp. 204-211 (2008).
Goodman and Gilman's, "The Pharmacological Basis of Therapeutics" published by the McGraw-Hill Companies, Inc. pp. 5-8, 2001.
Gradishar, W.J. (2006) Albumin-bound paclitaxel: a next-generation taxane. Expert Opinion in Pharmacotherapy, vol. 7, No. 8, p. 1041-1053.
Gray et al., "Heparin and Low-molecular-weight heparin" Thromb. Haemost vol. 99, pp. 807-818 (2008).
Halsall et al., "Oxidation of Carbohydrate by the Periodate Ion" Journal of Chemical Society, 172:1427-1432 (1947).
He Zhou et al., "M-ONC 402—a non anticoagulant low molecular weight heparin inhibits tumor metastasisHe", Proceedings of the American Association for Cancer Research Annual Meeting, p. 69 (2009).
Hilbe, et al., "CD133 positive endothelial progenitor cells contribute to the tumour vasculature in non-small cell lung cancer" J Clin Pathol, 57:965-969 (2004).
Hrivocíni, et al., "Active Conformation of Glycosaminoglycans. NMR Determination of the Conformation of Heparin Sequences Complexed with Antithrombin and Fibroblast Growth Factors in Solution", Seminars in Thrombosis and Hemostasis, vol. 28, No. 4, pp. 325-333 (2002).
Icli et al., "Low moelecular weight heparin (LMWH) increase the efficacy of cisplatinum plus gemcitabine combination in advanced pancreatic cancer", J. Surg Oncol., vol. 95 (6), pp. 507-512 (2007) Abstract Only
International Preliminary Report on Patentability for PCT/US2008/082223 filing date Nov. 3, 2008.
International Prelimnary Report of Patentability and Written Opinion from International Application Serial No. PCT/US2008/082224 dated Feb. 4, 2010.

(56) References Cited

OTHER PUBLICATIONS

International Prelimnary Report of Patentability and Written Opinion from International Application Serial No. PCT/US2010/031480 dated Oct. 18, 2011.
International Prelimnary Report of Patentability and Written Opinion from International Application Serial No. PCT/US2011/032581 dated Oct. 16, 2012.
International Prelimnary Report of Patentability and Written Opinion from International Application Serial No. PCT/US2011/032771 dated Oct. 16, 2012.
International Search Report for PCT/US2008/082223 dated Jan. 28, 2009.
International Search Report for PCT/US2008/082224 dated May 20, 2009.
International Search Report for PCT/US2010/031480 dated Sep. 27, 2010.
International Search Report for PCT/US2011/032581 dated Jul. 5, 2011.
International Search Report for PCT/US2011/32581 dated Jul. 5, 2011.
International Search Report for PCT/US2011/32771 dated Nov. 23, 2011.
International Search Report for PCT/US2014/039538 dated Oct. 1, 2014.
International Search Report for PCT/US2014/039542 dated Oct. 1, 2014.
International Search Report including Written Opinion for PCT/US2011/040470 dated Oct. 16, 2012.

\* cited by examiner

PHARMACEUTICAL COMPOSITIONS

CROSS-REFERENCE TO RELATED APPLICATIONS

This application is a national stage application under 35 U.S.C. § 371 International Application No.: PCT/US2014/039542, filed May 27, 2014, which claims the benefit under 35 U.S.C. 0 119(e) of United States provisional application 61/828,116, filed May 28, 2013.

BACKGROUND

This disclosure relates to therapeutic and/or diagnostic formulations with altered, optimized, and/or improved characteristics.

SUMMARY OF THE INVENTION

In one aspect, described herein are pharmaceutical compositions comprising a LMWH preparation having at least one chain having a glycol split uronic acid residue ($U_G$) in the preparation (e.g., a glycol split LMWH preparation described herein, e.g., an M402 preparation); and one or more buffering agents (e.g., one or more buffering agents described herein (e.g., a citrate buffer, a phosphate buffer, a histidine buffer, a maleate buffer, a succinate buffer, an acetate buffer, or any combination thereof)). In some embodiments, the pharmaceutical composition further comprises one or more bulking agents (e.g., a bulking agent described herein, e.g., a polyol, e.g., mannitol).

In some embodiments, the pH of the composition is between about 4.0-9.0 (e.g., between about 6.0-7.0, e.g., 6.2, 6.3, 6.4, or 6.5). In some embodiments, formic acid is detectable in the composition but at less than 2%, 1%, 0.5%, 0.3%, 0.2%, 0.1%, 0.05%, as determined by 1D-NMR and/or $C_2H_6O_3$ is detectable in the composition but at less than 2%, 1%, 0.5%, 0.3%, 0.2%, 0.1%, 0.05%, as determined by 2D-NMR. In some embodiments, the LMWH preparation is an M402 preparation. In some embodiments, the LMWH preparation is any combination thereof. In some embodiments, the pharmaceutical composition further comprises one or more alcohol (e.g., benzyl alcohol, e.g., 15 mg/mL benzyl alcohol). In some embodiments, the pharmaceutical composition further comprises one or more antioxidant (e.g., alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite).

In one aspect, described herein are pharmaceutical compositions comprising a LMWH preparation having at least one chain having a glycol split uronic acid residue ($U_G$) in the preparation (e.g., a LMWH preparation described herein, e.g., an M402 preparation); and a citrate buffer. In some embodiments, the pharmaceutical composition further comprises one, two, three, four, five, or six of a phosphate buffer, a histidine buffer, a succinate buffer, an acetate buffer, and/or a malate buffer. In some embodiments, the citrate buffer is about 5 to 40 mM, e.g., 10-30 mM. In some embodiments, the pharmaceutical composition further comprises an antioxidant, e.g., ascorbic acid. In some embodiments, the pH of the composition is about 5.5 to 6.5. In one aspect, the disclosure features an article of manufacture, e.g., a container or vial, containing a pharmaceutical composition described herein. In one embodiment, the article of manufacture, e.g., the container or vial, comprises an anaerobic overlay, e.g., an overlay described herein, e.g., a nitrogen overlay.

In one aspect, described herein are pharmaceutical compositions comprising a LMWH preparation having at least one chain having a glycol split uronic acid residue ($U_G$) in the preparation (e.g., a LMWH preparation described herein, e.g., an M402 preparation); and a histidine buffer. In some embodiments, the pharmaceutical composition further comprises one, two, three, four, five, or six of a citrate buffer, phosphate buffer, a succinate buffer, an acetate buffer, and/or a malate buffer. In some embodiments, the histidine buffer is about 5 to 40 mM, e.g., 10-30 mM. In some embodiments, the pharmaceutical composition further comprises an anti-

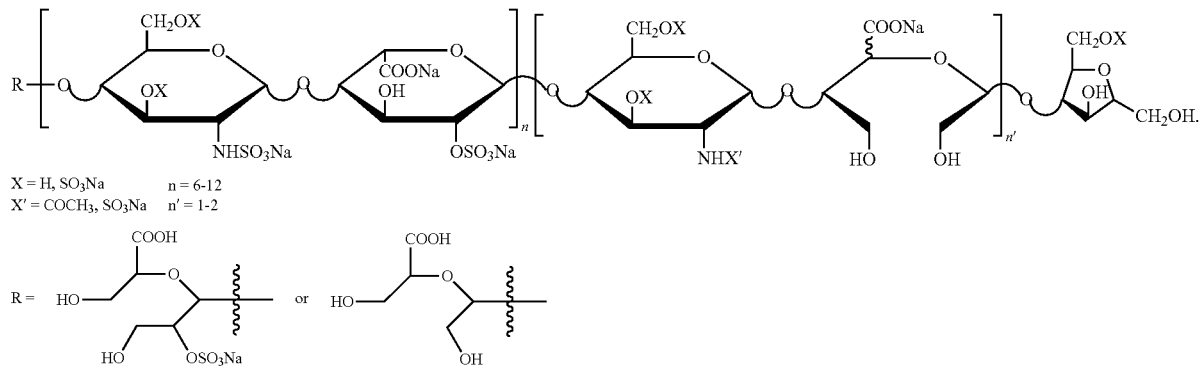

In some embodiments, the pharmaceutical composition contains about 150 mg mL$^{-1}$ of the LMWH preparation. In some embodiments, the buffering agent is a citrate buffer (e.g., a sodium citrate buffer, e.g., 5-40 mM sodium citrate, e.g., 10-30 mM sodium citrate), a phosphate buffer (e.g., phosphate citrate, sodium phosphate), a histidine buffer (e.g., 5-40 mM histidine, e.g., 10-30 mM histidine), a maleate buffer (e.g., 5-40 mM maleate buffer, e.g., 10-30 mM maleate buffer), a succinate buffer, an acetate buffer, or oxidant, e.g., ascorbic acid. In some embodiments, the pH of the composition is about 6.5 to 7.5. In one aspect, the disclosure features an article of manufacture, e.g., a container or vial, containing a pharmaceutical composition described herein. In one embodiment, the article of manufacture, e.g., the container or vial, comprises an anaerobic overlay, e.g., an overlay described herein, e.g., a nitrogen overlay.

In one aspect, described herein are pharmaceutical compositions comprising a LMWH preparation having at least one chain having a glycol split uronic acid residue ($U_G$) in the preparation (e.g., a LMWH preparation described herein, e.g., an M402 preparation); and a maleate buffer. In some

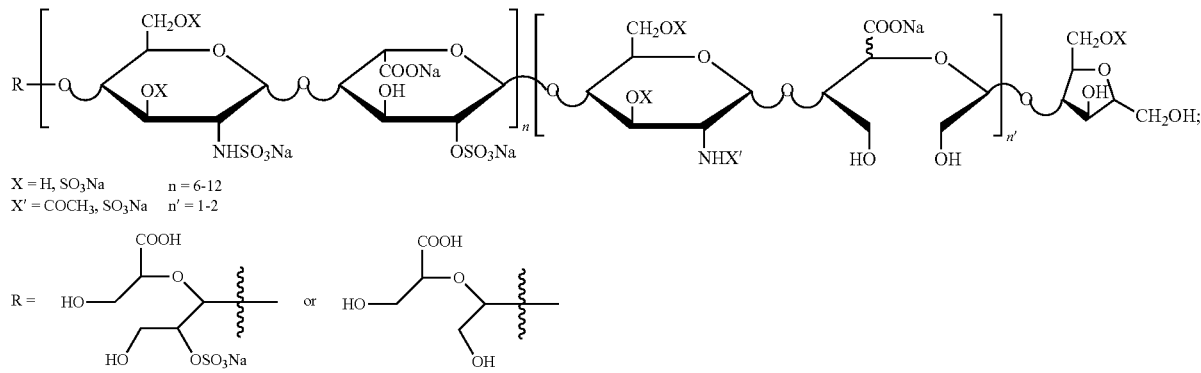

embodiments, the pharmaceutical composition further comprises one, two, three, four, five, or six of a citrate buffer, phosphate buffer, a histidine buffer, a succinate buffer, and/or an acetate buffer. In some embodiments, the maleate buffer is about 5 to 40 mM, e.g., 10-30 mM. In some embodiments, the pH of the composition is about 6.5 to 7.5. In one aspect, the disclosure features an article of manufacture, e.g., a container or vial, containing a pharmaceutical composition described herein. In one embodiment, the article of manufacture, e.g., the container or vial, comprises an anaerobic overlay, e.g., an overlay described herein, e.g., a nitrogen overlay.

In one aspect, described herein are pharmaceutical compositions comprising a LMWH preparation having at least one chain having a glycol split uronic acid residue ($U_G$) in the preparation (e.g., a LMWH preparation described herein, e.g., an M402 preparation); and a phosphate buffer. In some embodiments, the pharmaceutical composition further comprises one, two, three, four, five, or six of a citrate buffer, a histidine buffer, a succinate buffer, an acetate buffer, and/or a malate buffer. In some embodiments, the phosphate buffer is about 5 to 40 mM, e.g., 10-30 mM. In some embodiments, the pH of the composition is about 6.0 to 8.0, e.g., about 7.5. In some embodiments, the pharmaceutical composition further comprises an antioxidant, e.g., ascorbic acid. In one aspect, the disclosure features an article of manufacture, e.g., a container or vial, containing a pharmaceutical composition described herein. In one embodiment, the article of manufacture, e.g., the container or vial, comprises an anaerobic overlay, e.g., an overlay described herein, e.g., a nitrogen overlay.

In one aspect, described herein are pharmaceutical compositions comprising a LMWH preparation having at least one chain having a glycol split uronic acid residue ($U_G$) in the preparation (e.g., a LMWH preparation described herein, e.g., an M402 preparation); and an acetate buffer. In some embodiments, the pharmaceutical composition further comprises one, two, three, four, five, or six of a citrate buffer, a histidine buffer, a succinate buffer, a phosphate buffer, and/or a malate buffer. In some embodiments, the pharmaceutical composition further comprises an antioxidant, e.g., ascorbic acid. In one aspect, the disclosure features an article of manufacture, e.g., a container or vial, containing a pharmaceutical composition described herein. In one embodiment, the article of manufacture, e.g., the container or vial, comprises an anaerobic overlay, e.g., an overlay described herein, e.g., a nitrogen overlay.

In one aspect, described herein are pharmaceutical compositions comprising:

and one or more buffering agents (e.g., one or more buffering agents described herein (e.g., a citrate buffer, a phosphate buffer, a histidine buffer, a maleate buffer, a succinate buffer, an acetate buffer, a malate buffer, or any combination thereof).

In some embodiments, formic acid is detectable in the composition but at less than 2%, 1%, 0.5%, 0.3%, 0.2%, 0.1%, 0.05%, as determined by 1D-NMR and/or $C_2H_6O_3$ is detectable in the composition but at less than 2%, 1%, 0.5%, 0.3%, 0.2%, 0.1%, 0.05%, as determined by 2D-NMR.

In one aspect, the disclosure features an article of manufacture, e.g., a container or vial, containing a pharmaceutical composition described herein. In one embodiment, the article of manufacture, e.g., the container or vial, comprises an anaerobic overlay, e.g., an overlay described herein, e.g., a nitrogen overlay.

In one aspect, described herein methods of administering a pharmaceutical composition described herein, e.g., by intravenous or subcutaneous administration, to a subject. In one aspect, described herein methods of treating a subject having a disorder with a pharmaceutical composition described herein. In one aspect, described herein methods of treating a subject with a pharmaceutical composition described herein wherein the subject is treated for a disorder described herein.

In one aspect, described herein methods for manufacturing a M402 preparation, the method comprising: obtaining a first polysaccharide preparation comprising unfractionated heparin; depolymerizing the first polysaccharide preparation for a time and under conditions to obtain a second polysaccharide preparation having a weight average molecular weight of 3-8 kDa; modifying the second polysaccharide preparation to obtain a third polysaccharide preparation comprising at least one chain having a glycol split uronic acid residue formulating the third polysaccharide preparation with the third polysaccharide preparation with one or more buffering agent (e.g., one or more buffering agents described herein (e.g., a citrate buffer, a phosphate buffer, a histidine buffer, a maleate buffer, a succinate buffer, an acetate buffer, a malate buffer, or any combination thereof)), to thereby manufacture a LMWH (e.g., a glycol split LMWH, e.g., M402).

In some embodiments, the first polysaccharide preparation is depolymerized using nitrous acid based depolymerization. In some embodiments, the second polysaccharide preparation is modified by subjecting the second polysaccharide preparation periodate oxidation. In some embodiments, the method further comprises purifying the third polysaccharide preparation, e.g., by a chromatographic method (e.g. gel filtration chromatography). In some embodiments, the method further comprises reducing the third polysaccharide preparation, e.g., by treatment with a reducing agent (e.g., sodium borohydride).

In one aspect, described herein methods for manufacturing a M402 preparation, the method comprising: (a) obtaining a preparation of unfractionated heparin (UFH); (b) depolymerizing the UFH for a time and under conditions to obtain a first LMWH preparation having a weight average molecular weight of 3000-8000 Da; (c) glycol splitting the first LMWH preparation to obtain a second LMWH preparation; (d) reducing and purifying the second LMWH preparation; (e) formulating the second LMWH preparation with one or more buffering agent (e.g., one or more buffering agents described herein (e.g., a citrate buffer, a phosphate buffer, a histidine buffer, a maleate buffer, a succinate buffer, an acetate buffer, a malate buffer, or any combination thereof)), to thereby manufacture a M402 preparation.

Compositions described herein include, inter alia, pharmaceutical compositions, e.g., formulations, comprising a LMWH preparation having at least one chain having a glycol split uronic acid residue ($U_G$) in the preparation (e.g., a glycol split LMWH preparation described herein, e.g., an M402 preparation); and one or more buffering agent (e.g., one or more buffering agents described herein (e.g., a citrate buffer, a phosphate buffer, a histidine buffer, a maleate buffer, a succinate buffer, an acetate buffer, a malate buffer, or any combination thereof)). In some embodiments, the glycol split LMWH preparation is a LMWH preparation disclosed in WO2011/130572, which is hereby incorporated by reference with respect to any disclosure relating to a LWMH. In some embodiments, the glycol split LMWH preparation comprises a polysaccharide of Formula (I)

each X' is independently COCH$_3$ or SO$_3$Y;

each Y is independently a singularly charged cation such as Na$^+$, K$^+$, or NH$_4^+$;

n is an integer from 5 to 14, e.g., 6 to 12;

n' is 1, 2 or 3, e.g., 1 or 2; and

R is

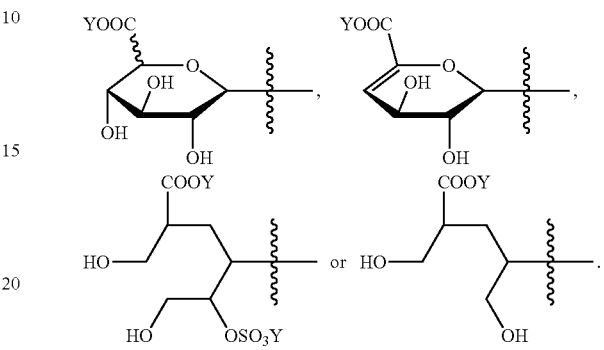

In some embodiments, the compound of Formula (I) is a compound of Formula (Ia)

Formula (Ia)

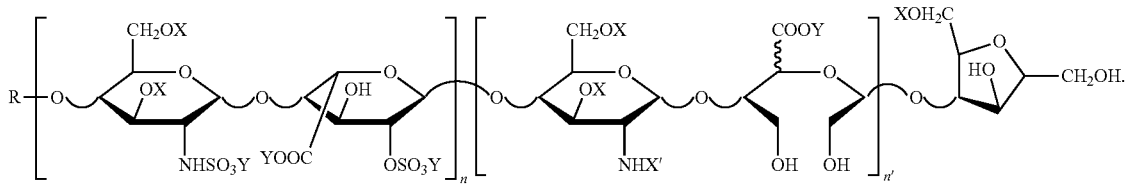

In some embodiments, Y for each occurrence is Na$^+$.

In some embodiments, R is

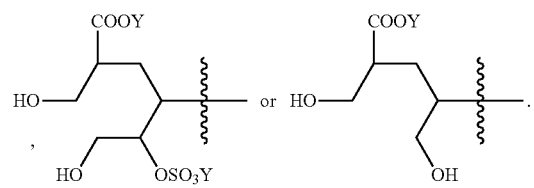

In some embodiments, the glycol split LMWH preparation has the following characteristics:

Formula (I)

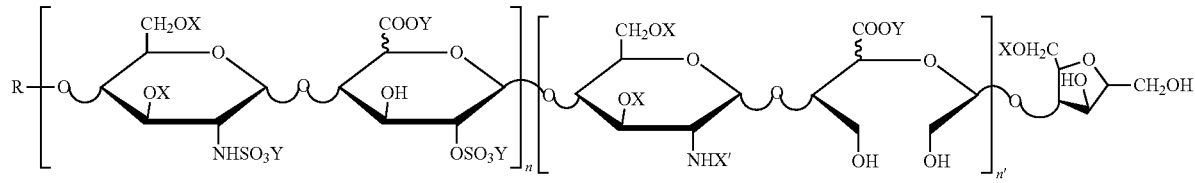

wherein, each X is independently H or SO$_3$Y;

(a) a weight average chain molecular weight between 3,500 and 8,000 Da;

(b) anti-Xa activity of less than 20 IU/mg and anti-IIa activity of 1 IU/mg or less;
(c) greater than 5% and less than 25% glycol split uronic acid residues; and
(d) the polysaccharide preparation has a molecular weight distribution such that 10-40% of the oligosaccharides of the preparation have a molecular weight <3000 Da; 45-65% of the oligosaccharides have a molecular weight between 3000-8000 Da, and 15-30% of the oligosaccharides have a molecular weight >8000 Da.

In some embodiments, the LMWH preparation (e.g., the M402 preparation) has a molecular weight distribution such that 10-40% of the oligosaccharides of the preparation have a molecular weight <3000 Da; 45-65% of the oligosaccharides have a molecular weight between 3000-8000 Da, and 15-30% of the oligosaccharides have a molecular weight >8000 Da.

In some embodiments, the glycol split LMWH preparation has the following characteristics:
(a) a weight average chain molecular weight between 2,000 and 10,000 Da, e.g., 3,000 and 10,000; 3,500 and 10,000; 3,000 and 9,000, 3,500 and 9,000; 3,000 and 8,500; 3,500 and 8,500; 3,000 and 8,000; or 3,500 and 8,000;
(b) anti-Xa activity of less than 20 IU/mg and anti-IIa activity of 20 IU/mg or less;
(c) greater than 5% and less than 25% glycol split uronic acid residues; and
(d) the polysaccharide preparation has a molecular weight distribution such that 5-50%, e.g., 10-40%, of the oligosaccharides of the preparation have a molecular weight <3000 Da; 35-75%, e.g., 45-65%, of the oligosaccharides have a molecular weight between 3000-8000 Da, and 5-50%, e.g., 15-30%, of the oligosaccharides have a molecular weight >8000 Da.

In some embodiments, the LMWH preparation is an M402 preparation. In some embodiments, the M402 preparation is Necuparinol.

In some embodiments, the glycol split LMWH preparation comprises or consists essentially of:

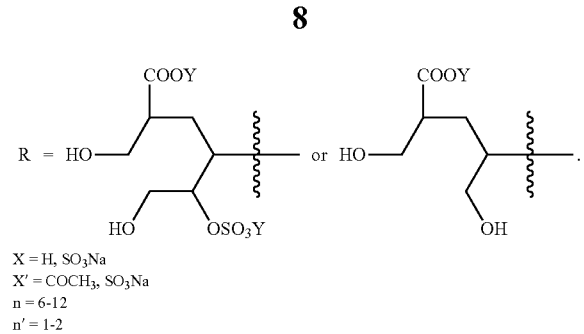

$X = H, SO_3Na$
$X' = COCH_3, SO_3Na$
$n = 6-12$
$n' = 1-2$

In some embodiments, the pharmaceutical composition contains about 150 mg mL$^{-1}$ of the LMWH preparation. In some embodiments, the buffering agent is a citrate buffer (e.g., a sodium citrate buffer, e.g., 5-20 mM sodium citrate, e.g., 10 mM sodium citrate), a phosphate buffer (e.g., phosphate citrate), a histidine buffer, a maleate buffer, a succinate buffer, an acetate buffer, or any combination thereof. In some embodiments, the pharmaceutical composition further comprises one or more alcohol (e.g., benzyl alcohol, e.g., 15 mg/mL benzyl alcohol). In some embodiments, the pharmaceutical composition further comprises one or more antioxidant (e.g., alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite).

In some embodiments, the pharmaceutical composition further comprises one or more bulking agents (e.g., a bulking agent described herein, e.g., a polyol, e.g., mannitol). In some embodiments, the pH of the composition is between about 4.0-9.0 (e.g., between about 6.0-7.0, e.g., 6.2, 6.3, 6.4, or 6.5).

In some aspects, the disclosure features a pharmaceutical composition comprising a LMWH preparation having at least one chain having a glycol split uronic acid residue ($U_G$) in the preparation (e.g., a glycol split LMWH preparation described herein, e.g., an M402 preparation); and a citrate buffer, e.g., at about 5 to 40 mM, e.g., 10-30 mM.

In one embodiment, the pharmaceutical composition further comprises an antioxidant, e.g., ascorbic acid.

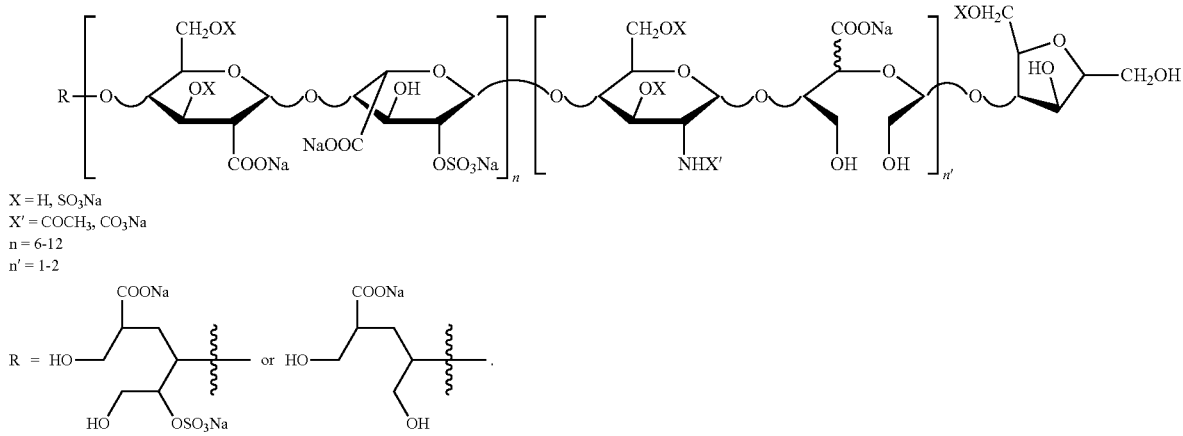

$X = H, SO_3Na$
$X' = COCH_3, CO_3Na$
$n = 6-12$
$n' = 1-2$ which is also represented as:

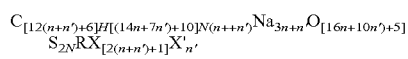

$C_{[12(n+n')+6]}H_{[(14n+7n')+10]}N_{(n++n')}Na_{3n+n}O_{[16n+10n')+5]}$
$S_{2N}RX_{[2(n+n')+1]}X'_{n'}$

In one embodiment, the pH of the pharmaceutical composition is about 5.5 to 6.5.

In one aspect, the disclosure features a pharmaceutical composition comprising a LMWH preparation having at least one chain having a glycol split uronic acid residue ($U_G$) in the preparation (e.g., a glycol split LMWH preparation described herein, e.g., an M402 preparation); and a histidine buffer, e.g., at about 5 to 40 mM, e.g., 10-30 mM.

In one embodiment, the pharmaceutical composition further comprises an antioxidant, e.g., ascorbic acid.

In one embodiment, the pH of the composition is about 6.5 to 7.5.

In one aspect, the disclosure features a pharmaceutical composition comprising a LMWH preparation having at least one chain having a glycol split uronic acid residue ($U_G$) in the preparation (e.g., a glycol split LMWH preparation described herein, e.g., an M402 preparation); and a maleate buffer, e.g., at about 5 to 40 mM, e.g., 10-30 mM.

In one embodiment, the pH of the composition is about 6.5 to 7.5.

In one aspect, the disclosure features a pharmaceutical composition comprising a LMWH preparation having at least one chain having a glycol split uronic acid residue ($U_G$) in the preparation (e.g., a glycol split LMWH preparation described herein, e.g., an M402 preparation); and a phosphate buffer, e.g., at about 5 to 40 mM, e.g., 10-30 mM.

In one embodiment, the pH of the composition is about 6.0 to 8.0, e.g., about 7.5.

In one aspect, the disclosure features an article of manufacture, e.g., a container or vial, containing a pharmaceutical composition described herein. In one embodiment, the article of manufacture, e.g., the container or vial, comprises an anaerobic overlay, e.g., an overlay described herein, e.g., a nitrogen overlay.

Also described herein are, inter alia, methods of administering a pharmaceutical composition described herein, e.g., by intravenous or subcutaneous administration, to a subject.

In certain aspects, described herein are methods of treating a subject having a disorder with a pharmaceutical composition described herein (e.g., a glycol split LMWH preparation described herein, e.g., an M402 preparation).

In certain aspects, described herein are methods of treating a subject with a pharmaceutical composition described herein (e.g., a glycol split LMWH preparation described herein, e.g., an M402 preparation), wherein the subject is treated for a disorder described herein, e.g., a metastatic disorder, e.g., a cancer.

Described herein are, inter alia, pharmaceutical compositions comprising a low molecular weight heparin (LMWH) preparation having at least one chain having a glycol split uronic acid residue ($U_G$) in the preparation (e.g., a LMWH preparation described herein, e.g., an M402 preparation) and one or more buffering agents (e.g., one or more buffering agents described herein). In some instances, the pH of the composition is between about 4.0-9.0, and/or the composition is substantially free of formic acid (e.g., less than 2%, 1%, 0.5%, 0.1%, 0.05%, or 0.01%, formic acid, e.g., as determined by 1D-NMR and/or formic acid is undetectable by 1D NMR, wherein % refers to w/w or mol/mol) and/or $C_2H_6O_3$ (e.g., less than 2%, 1%, 0.5%, 0.1%, 0.05% $C_2H_6O_3$, e.g., as determined by 2D-NMR, and/or $C_2H_6O_3$ is undetectable by 2D-NMR, wherein % refers to w/w or mol/mol).

Also described herein are methods of making and using such pharmaceutical compositions. Such methods include, inter alia, methods of administering a pharmaceutical composition described herein, e.g., by intravenous or subcutaneous administration, to a subject, and methods of treating a subject having a disorder (e.g., a disorder described herein) with a pharmaceutical composition described herein. Exemplary disorders include, but are not limited to a proliferative disorder, e.g., a VEGF, FGF, SDF-α and/or selectin mediated proliferative disorder, a cancer (e.g., a cancer described herein), a metastatic cancer, an inflammatory disease, an infectious disease, an autoimmune disease, or fibrosis. Also described are articles of manufacture and kits comprising the described pharmaceutical compositions.

LMWH Preparations

The pharmaceutical compositions described herein include a LMWH preparation having at least one chain having a glycol split uronic acid residue ($U_G$) in the preparation. In certain embodiments, the LMWH preparation is a LMWH preparation described in more detail below. For example, the glycol split LMWH preparation is a glycol split LMWH preparation described herein that lacks substantial anti-Xa activity and/or anti-IIa activity, e.g., anti-IIa activity less than 50 IU/mg (e.g., anti-IIa activity less than 1 IU/mg) and/or anti-Xa activity less than 50 IU/mg (e.g., anti-Xa activity less than 20 IU/mg or less, e.g., 10 IU/mg or less). In certain embodiments, the glycol split LMWH preparation is a LMWH preparation described herein that has (a) a weight average chain molecular weight between 3,500 and 8,000 Da; (b) anti-Xa activity of less than 20 IU/mg and anti-IIa activity of 1 IU/mg or less; (c) greater than 5% and less than 25% glycol split uronic acid residues; and (d) the polysaccharide preparation has a molecular weight distribution such that 10-40% of the oligosaccharides of the preparation have a molecular weight <3000 Da; 45-65% of the oligosaccharides have a molecular weight between 3000-8000 Da, and 15-30% of the oligosaccharides have a molecular weight >8000 Da.

In certain embodiments, the glycol split LMWH preparation is an M402 preparation. In one embodiment, the M402 preparation has a molecular weight distribution such that 10-40% of the oligosaccharides of the preparation have a molecular weight <3000 Da; 45-65% of the oligosaccharides have a molecular weight between 3000-8000 Da, and 15-30% of the oligosaccharides have a molecular weight >8000 Da.

In some embodiments, the compositions described herein contain the LMWH preparation at about 150 mg mL$^{-1}$. In some embodiments, the compositions described herein contain the LMWH preparation in an amount less than 150 mg mL$^{-1}$. In some embodiments, the compositions described herein contain LMWH preparation in an amount greater than 150 mg mL$^{-1}$. In some embodiments, the compositions described herein contain an M402 preparation in an amount between 1-500 mg mL$^{-1}$, e.g., 1, 10, 50, 75, 100, 125, 175, 200, 225, 250, 275, 300, 325, 350, 375, 400, 425, 450, or 500 mg mL$^{-1}$. In some embodiments, the compositions described herein contain LMWH preparation in an amount greater than 1 mg mL$^{-1}$. In an embodiment, the compositions described herein contain LMWH preparation in an amount less than 500 mg mL$^{-1}$. In an embodiment, the preparations described herein contain LMWH preparation in an amount less than 450 mg mL$^{-1}$.

DEFINITIONS

Stability

A "stable" LMWH preparation, as used herein, is a preparation that is substantially free from a degradation product. "Substantially free from a degradation product" means that the preparation contains less than 1%, 0.5%, 0.1%, 0.05%, 0.02%, 0.01%, 0.001% weight/weight (w/w) formic acid as determined by 1D-NMR, or levels of formic acid that are undetectable by 1D NMR. NMR, including 1D NMR, methods suitable for use herein are disclosed in U.S. Ser. No.: 61/828,106, which application and/or methods are hereby incorporated by reference.

In some embodiments, a composition described herein can include a preservative. A "preservative" as used herein is a compound which can be added to essentially reduce bacterial action in the composition. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, phenolic compounds, bisphenol, butyl and benzyl alcohol, allyl parabens such as methyl or propyl paraben, catechol, resorcinol, cyclohexanol, 3-pentanol, and m-cresol. In some embodiments, the preservative is benzyl alcohol. Other suitable alcohols can include, but are not limited to ethanol, polyethylene glycol, chlorobutanol, hydroxybenzoate, and/or phenylethyl alcohol.

In some embodiments, a composition described herein includes a tonicity agent. A "tonicity agent" as used herein is a compound which renders the formulation isotonic.

A "polyol" is a substance with multiple hydroxyl groups, and includes sugars (reducing and nonreducing sugars), sugar alcohols and sugar acids. Preferred polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "nonreducing sugar" is one which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. The polyol may also act as a tonicity agent. In one embodiment, one ingredient of the formulation is mannitol in a concentration of 5 to 20 mg/ml. In an embodiment of the invention, the concentration of mannitol is 7.5 to 15 mg/ml. In an embodiment, the concentration of mannitol is 10-14 mg/ml. A polyol, which can act as a tonicifier and may stabilize the LMWH preparation, can be included in a composition described herein. The polyol is added to the formulation in an amount which may vary with respect to the desired isotonicity of the composition. In some embodiments, the aqueous formulation is isotonic. The amount of polyol added may also alter with respect to the molecular weight of the polyol. For example, a lower amount of a monosaccharide (e.g. mannitol) may be added, compared to a disaccharide (such as trehalose).

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

A "diluent" as used herein is an agent which is pharmaceutically acceptable (safe and non-toxic for administration to a human) and is useful for the preparation of a reconstituted composition. Exemplary diluents include sterile water, bacteriostatic water for injection (BWFI), a pH buffered solution (e.g. phosphate-buffered saline), sterile saline solution, Ringer's solution or dextrose solution.

A "bulking agent," as used herein, is a compound which adds mass to a lyophilized mixture (such as a dry composition described herein) and can contribute to the physical structure of the lyophilized material such as a lyophilized cake (e.g. facilitates the production of an essentially uniform lyophilized cake which maintains an open pore structure). Exemplary bulking agents include mannitol, glycine, polyethylene glycol and xorbitol. In some embodiments, the bulking agent is mannitol. In one embodiment, the pharmaceutical composition contains between about 1 and about 20 mg/ml of mannitol as determined in a reconstituted form such as a pharmaceutical composition described herein, for example, between about 5 and about 15 mg/ml (e.g., about 10 or about 12 mg/ml). A "buffer" as used herein is an agent that maintains a stable pH in a solution within a specific pH range. Buffering ranges are determined by pKa. An aqueous formulation can be prepared including the therapeutic agent in a pH-buffered solution. In some embodiments, a composition described herein includes a buffering agent. Examples of potential buffering agents include a citrate buffer, a phosphate buffer, a histidine buffer, a maleate buffer, a succinate buffer, an acetate buffer, a malate buffer, or any combination thereof.

An "antioxidant" as described herein is a compound that functions to reduce oxidation of a species within the LMWH preparation, e.g., aldehydes, within the composition. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite.

As used herein, "pH" or "pKa" units or values can include +/−0.5 (e.g., 0.1, 0.2, 0.3, 0.4, 0.5, 1.0, 2.0, 2.5) units. As used herein, "pH" or "pKa" units or values can include +/−0.5 (e.g., 0.1, 0.2, 0.3, 0.4, 0.5, 1.0, 2.0, 2.5) units at a predetermined temperature, e.g., 0-50° C.

The terms "treating", "treatment", and the like, mean administering the composition to a subject or a cell or tissue of a subject in order to obtain a desired pharmacological, physiological or clinical effect. Treatment with a pharmaceutical composition described herein may lessen, reduce, mitigate, ameliorate, delay, or prevent an existing unwanted condition or the onset or a symptom thereof. A "therapeutically effective amount" refers to an amount effective, at dosages and for periods of time necessary, to achieve the desired pharmacological, physiological or clinical effect in the subject.

A person of ordinary skill in the art will appreciate that assessment of stability is not limited to the methods disclosed herein and need not be expressed using the units or metrics disclosed herein. For example, other analytical techniques that can be used to measure stability are available in the art and can include, but are not limited to, GPC, GPC-MS, LC-MS, IP RPHPLC. Various analytical techniques that can be used are reviewed, for example, as described in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Nevertheless, comparison of stability will be conducted using the methods, units, and/or metrics disclosed herein. More specifically, an assessed stability is equivalent to those disclosed herein as long as the assessed stability meets the herein disclosed stability when the herein disclosed methods, units and/or metrics are used, e.g., allowing for the sensitivity (e.g., analytical variability) of the method being used to measure the value.

DETAILED DESCRIPTION

Described herein are pharmaceutical compositions, comprising a LMWH preparation, formulated in a manner to optimize the structural (e.g., chemical) integrity of the LMWH preparation, e.g., formulated such that stability of the LMWH preparation is provided and/or improved.

Due to certain structural/chemical and functional attributes, heparins and low molecular weight heparins are generally formulated in water only (see, e.g., enoxaparin, a generic Lovenox®). For example, heparins are generally considered to be stable; consequently heparin compositions do not typically include buffers to maintain stability. Similarly, heparins are structurally bulky, thus, heparin compositions do not typically include bulking agents. In addition, heparins are known to have high osmolarity (a characteristic relevant for administration because high osmolarity can result in injection-site irritation (most drugs are formulated with isotonic osmolarity, e.g., about 280-300 mOsm/L), which is optimal for administration), thus including a bulking agent, such as mannitol, in a heparin composition would reasonably be expected to increase the osmolarity of the composition, which would generally be regarded as undesirable. This disclosure is based, at least in part, on the discovery that low molecular weight heparins having at least one chain having a glycol split uronic acid residue ($U_G$) in the preparation (e.g., glycol split LMWH), such as an M402 preparation, are sensitive to degradation, e.g., under certain types of stress. For example, as shown herein, M402 subjected to accelerating storage conditions commonly used to reduce shelf-life of a therapeutic product (e.g., increased temperature, increased moisture, altered pH) had a tendency to exhibit signs of reduced shelf-life, e.g., as assessed by various criteria including, color, pH, aggregation, precipitation Certain of such samples also exhibited reduced stability. In contrast, compositions or formulations described herein were found to provide and/or improve LMWH stability, e.g., under accelerating conditions representative of long term storage. Accordingly, compositions disclosed herein can provide and/or improve stability of glycol split LMWH preparations at or following exposure of the preparation to stress. In some instances, stress can include exposure of the preparation to accelerating storage conditions (e.g., exemplified herein) for 30, 60, 90, days, 1 year, and/or greater than 1 year. Alternatively or in addition, compositions or formulations described herein can provide and/or improve LMWH stability for defined time periods under standard storage conditions (e.g., atmospheric pressure, controlled light, ambient humidity, and/or at a temperature of 2-8° C.). With respect to M402 and without being limiting by theory, data suggest that chemistry used to generate M402 produces species, such as aldehydes, that are amenable to primary degradation pathways. Accordingly, the disclosure provides compositions comprising glycol split low molecular weight heparins formulated to preserve their structural (e.g., chemical) and/or functional integrity.

In some instances, low molecular weight heparins disclosed herein (e.g., glycol split LMWH) include diagnostic low molecular weight heparins and/or therapeutic low molecular weight heparins. In some instances, the disclosure provides compositions (e.g., pharmaceutical compositions) comprising a low molecular weight heparin (LMWH) preparation having at least one chain having a glycol split uronic acid residue ($U_G$) in the preparation (e.g., a LMWH preparation described herein, e.g., an M402 preparation) and one or more buffering agents (e.g., one or more buffering agents described herein). Also described herein are pharmaceutical compositions comprising a LMWH preparation having at least one chain having a glycol split uronic acid residue ($U_G$) in the preparation (e.g., a LMWH preparation described herein, e.g., an M402 preparation) and one or more bulking agent (e.g., a bulking agent described herein, e.g., a polyol, e.g., mannitol). In some instances, the pH of the composition is between about 4.0-9.0, and/or the composition is stable. In some instances, low molecular weight heparins include an M402 preparation, described below.

LMWH Preparations

The pharmaceutical compositions described herein include a low molecular weight heparin (LMWH) preparation having at least one chain having a glycol split uronic acid residue ($U_G$) in the preparation.

The disclosed pharmaceutical compositions include glycol split LMWH preparations designed to lack substantial anticoagulant activity while retaining clinically advantageous properties. Properties of the glycol split LMWH preparations include, e.g., lacking substantial anticoagulant activity, e.g., anti-IIa activity less than 50 IU/mg, anti-IIa activity less than 1 IU/mg anti-Xa activity less than 50 IU/mg, anti-Xa activity less than 10 IU/mg, and having anti-metastatic, anti-angiogenic, anti-fibrotic and/or anti-inflammatory activity.

In some embodiments, the LMWH preparation comprises at least one chain having a glycol split uronic acid residue ($U_G$) and, e.g., the preparation can lack substantial anticoagulant activity (e.g., preparations of polysaccharides that have reduced anticoagulant activity) but retain activity in other non-coagulation mediated biological processes. For example, these LMWH preparations can have one or more of the following features: 1) anti-Xa activity, e.g., less than 50 IU/mg, 20 IU/mg, 10 IU/mg, 5 IU/mg, 3 IU/mg, 2 IU/mg, 1 IU/mg or less, and 2) anti-metastatic, anti-angiogenic, anti-fibrotic and/or anti-inflammatory activity. A LMWH preparation provided herein can also have one or more of the following characteristics: the preparation has glycol split uronic acid residues ($U_G$) (e.g., less than 50%, 40%, 30%, 20% glycol split uronic acid residues ($U_G$)); the preparation has no more than 3 glycol split uronic acid residues ($U_G$) per polysaccharide chain; the preparation has greater than 40% $U_{2S}H_{NS,6S}$ disaccharide residues present in the chains of the preparation; the degree of desulfation of the preparation is less than 40%; one or more polysaccharide chains in the preparation have a 2,5-anhydromannitol residue at the reducing end. In some preferred embodiments, the weight average molecular weight of the preparation is between 3,500 and 8,000 Da, e.g., between 4,000 and 8,000 Da; and a molecular weight distribution such that 10-50% (e.g., 10-40%, 10-30%, 15-30% or 15-25%) of the oligosaccharides of the preparation have a molecular weight <3000 Da; 40-65% (e.g., 40-60%, 45-65%, 50-65%, or 55-65%) of the oligosaccharides have a molecular weight between 3000-8000 Da, and 5-30% (e.g., 10-30%, 15-30%, 10-25%, or 15-25%) of the oligosaccharides have a molecular weight >8000 Da.

In some embodiments, the LMWH preparation has a weight average molecular weight between 6,000 and 15,000 Da, e.g., between 10,000 and 14,000 Da. In other embodiments, the preparation has a weight average molecular weight between 3,000 and 8,000 Da.

Certain embodiments include a LMWH preparation having the following characteristics: (a) a weight average molecular weight between 3,500 and 8,000 Da, e.g., a weight average molecular weight described herein; (b) anti-Xa activity and/or anti-IIa activity, e.g., less than 50 IU/mg (e.g., anti-Xa activity less than about 40 IU/mg, 30 IU/mg, 20 IU/mg, 15 IU/mg, 10 IU/mg, 5 IU/mg, 4 IU/mg, 3 IU/mg, 2 IU/mg, or 1 IU/mg, and anti-IIa activity less than about 40 IU/mg, 30 IU/mg, 20 IU/mg, 10 IU/mg, 5 IU/mg, 4 IU/mg, 3 IU/mg, 2 IU/mg, or 1 IU/mg); and (c) less than 50% glycol split uronic acid residues (e.g., less than 40%, 30%, 25%, or 20% glycol split uronic acid residues but more than 1%, 5%, 10%, 15%) in the preparation. In some embodiments, the preparation contains between 5% and 50% glycol split uronic acid residues (e.g., between 5% and 40%, 5% and 30%, 10% and 50%, 10% and 40%, 10% and 30%, or 10 and 20% glycol split uronic acid residues). Preferably, the preparation has a molecular weight distribution such that 10-50% (e.g., 10-40%, 10-30%, 15-30% or 15-25%) of the oligosaccharides of the preparation have a molecular weight <3000 Da; 40-65% (e.g., 40-60%, 45-65%, 50-65%, or 55-65%) of the oligosaccharides have a molecular weight between 3000-8000 Da, and 5-30% (e.g., 10-30%, 15-30%, 10-25%, or 15-25%) of the oligosaccharides have a molecular weight >8000 Da.

Certain embodiments include a LMWH preparation having the following characteristics: (a) a weight average chain molecular weight between 3,500 and 8,000 Da; (b) anti-Xa activity of less than 20 IU/mg and anti-IIa activity of less than 20 IU/mg; and (c) greater than 5% and less than 25%, e.g., less than 20, less than 10, glycol split uronic acid residues. Certain embodiments include a LMWH preparation having the following characteristics: (a) a weight average chain molecular weight between 3,500 and 7,000 Da; (b) anti-Xa activity of less than 20 IU/mg and anti-IIa activity of less than 20 IU/mg; and (c) greater than 5% and less than 20% glycol split uronic acid residues.

Certain embodiments include a LMWH preparation having the following characteristics: (a) a weight average chain molecular weight between 3,500 and 8,000 Da; (b) anti-Xa activity of less than 20 IU/mg and anti-IIa activity of less than 20 IU/mg; and (c) greater than 5% and less than 25%, e.g., less than 20, less than 10, glycol split uronic acid residues; wherein the preparation has polysaccharide chains of the preparation having greater than 40%, e.g., greater than 50%, 60%,70%, $U_{2S}H_{NS,6S}$ disaccharide residues.

In some embodiments, the LMWH preparation has one or more chains having a glycol split uronic acid residue and each polysaccharide chain of the preparation having no more than 3, e.g., no more than 2, no more than 1, glycol split uronic acid residues ($U_G$). In some embodiments, the LMWH preparation has one or more chain having a glycol split uronic acid residue and each polysaccharide chain of the preparation having no more than 2 glycol split uronic acid residues ($U_G$). In some embodiments, the LMWH preparation has one or more chains having a glycol split uronic acid residue and each polysaccharide chain of the preparation having no more than 1 glycol split uronic acid residues ($U_G$).

In some embodiments, the LMWH preparation preparation has the following characteristics: (a) a weight average chain molecular weight between 3,500 and 8,000 Da; (b) anti-Xa activity of less than 20 IU/mg and anti-IIa activity of 1 IU/mg or less; (c) greater than 5% and less than 25% glycol split uronic acid residues; and (d) the polysaccharide preparation has a molecular weight distribution such that 10-40% of the oligosaccharides of the preparation have a molecular weight <3000 Da; 45-65% of the oligosaccharides have a molecular weight between 3000-8000 Da, and 15-30% of the oligosaccharides have a molecular weight >8000 Da.

In some embodiments, the LMWH preparation comprises a polysaccharide of Formula (I)

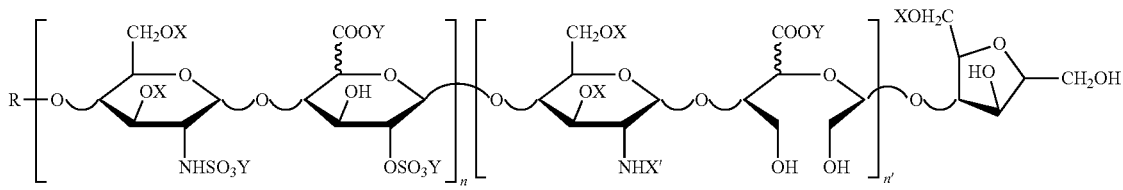

Formula (I)

wherein, each X is independently H or $SO_3Y$;

each X' is independently $COCH_3$ or $SO_3Y$;

each Y is independently a singularly charged cation such as $Na^+$, $K^+$, or $NH_4^+$;

n is an integer from 5 to 14, e.g., 6 to 12;

n' is 1, 2 or 3, e.g., 1 or 2; and

R is

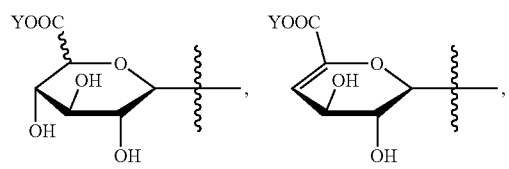

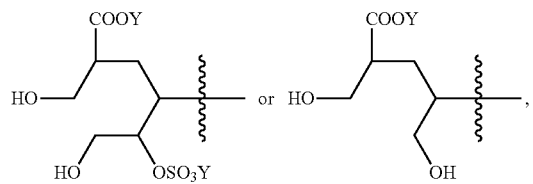

each Y is independently a singularly charged cation such as $Na^+$, $K^+$, or $NH_4^+$.

In some embodiments, the compound of Formula (I) is a compound of Formula (Ia)

Formula (Ia)

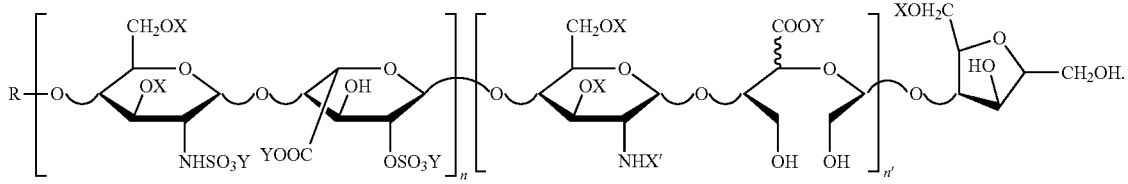

In some embodiments, Y for each occurrence is Na+.
In some embodiments, R is,

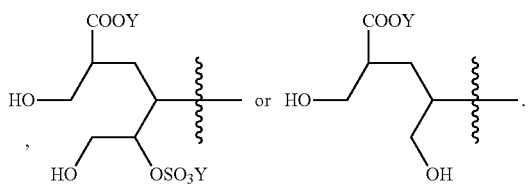

In some embodiments, the polysaccharide of Formula (I) is a polysaccharide of Formula (Ib)

Formula (Ib)

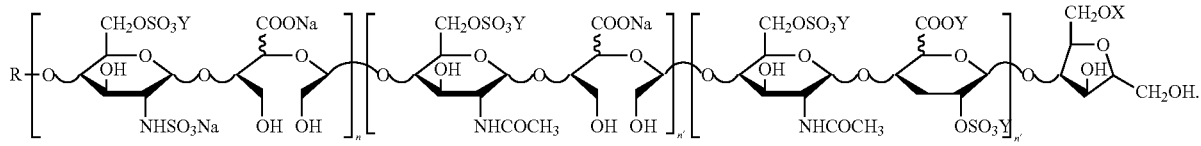

In some embodiments, Y for each occurrence is Na+.
In some embodiments, R is,

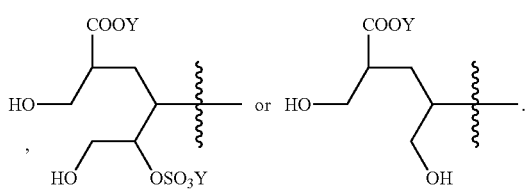

In some embodiments, at least about 20% (e.g., at least about 30%, at least about 40%, at least about 50%, at least about 60%, at least about 70%, at least about 80%, at least about 90%, at least about 95%, at least about 98%, or at least about 99%) of the polysaccharides in the preparation have the structure of Formula (I) or Formula (Ia).

Preferably, the preparation has anti-Xa activity of less than 50 IU/mg, 40 IU/mg, 30 IU/mg, 20 IU/mg or 10 IU/mg but greater than 0.5 IU/mg, 1 IU/mg and/or anti-IIa activity of less than 50 IU/mg, 40 IU/mg, 30 IU/mg, 20 IU/mg or 10 IU/mg but greater than 0.5 IU/mg, 1 IU/mg. In some embodiments, the preparation has a weight average chain molecular weight between 3,500 and 8,000 Da, e.g., between 4,000 and 8000 Da, 4,500 and 8,000 Da, 4,700 and 8,000 Da and 5,000 and 8,000 Da. In some embodiments, the preparation has a molecular weight distribution such that 10-50% (e.g., 10-40%, 10-30%, 15-30% or 15-25%) of the oligosaccharides of the preparation have a molecular weight <3000 Da; 40-65% (e.g., 40-60%, 45-65%, 50-65%, or 55-65%) of the oligosaccharides have a molecular weight between 3000-8000 Da, and 5-30% (e.g., 10-30%, 15-30%, 10-25%, or 15-25%) of the oligosaccharides have a molecular weight >8000 Da. The LMWH preparations described herein (e.g., described above) can also be a pharmaceutically acceptable salt of any of the LMWH preparations described herein.

Any of the preparations described herein, e.g., described above, can have other properties. E.g., one of the above described preparations can further have one or more of the functional or structural properties set out below:

the preparation or pharmaceutical preparation has a molecular weight distribution such that 10-50% (e.g., 10-40%, 10-30%, 15-30% or 15-25%) of the oligosaccharides of the preparation have a molecular weight <3000 Da; 40-65% (e.g., 40-60%, 45-65%, 50-65%, or 55-65%) of the oligosaccharides have a molecular weight between 3000-8000 Da, and 5-30% (e.g., 10-30%, 15-30%, 10-25%, or 15-25%) of the oligosaccharides have a molecular weight >8000 Da;

the preparation has a polydispersity of about 1.2 to 1.7 (e.g., about 1.3 to 1.7, 1.4 to 1.6, or 1.3 to 1.6);

the preparation has a polydispersity of about 1.2 to 1.8 (e.g., about 1.3 to 1.8, 1.4 to 1.7, or 1.3 to 1.7);

the preparation has a polydispersity of about 1.2 to 1.9 (e.g., about 1.3 to 1.9, 1.4 to 1.9, or 1.5 to 1.7);

the preparation or preparation has a sodium content less than 30%, 25%, 20%, 15%, 10%. In one embodiment, the preparation or preparation comprises: less than 20 ppm, 15 ppm, 10 ppm, 5 ppm iodine; less than 30%, 25%, 20%, 15%, 10% sulfur; less than 50, 40, 30, 20, 15 ppm boron;

the preparation or preparation has anti-metastatic activity;

the preparation or preparation binds specifically to or inhibits an activity of one or more of: VEGF, FGF, SDF-1-α, HB-EGF, heparanase, SCF, sonic hedgehog, osteopontin, osteopontegerin or P-selectin.

In some embodiments, the LMWH preparation is an M402 preparation. An "M402 preparation" refers to a LMWH preparation that consists essentially of:

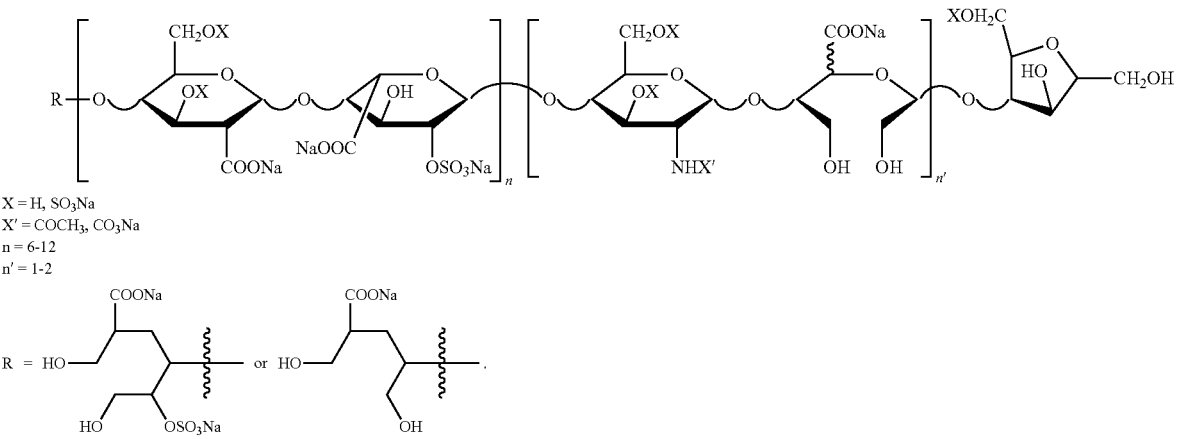

X = H, SO$_3$Na
X' = COCH$_3$, CO$_3$Na
n = 6-12
n' = 1-2

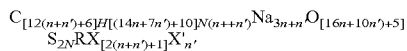

which is also represented as:

$C_{[12(n+n')+6]}H_{[(14n+7n')+10]}N_{(n++n')}Na_{3n+n}O_{[16n+10n')+5]}S_{2N}RX_{[2(n+n')+1]}X'_{n'}$

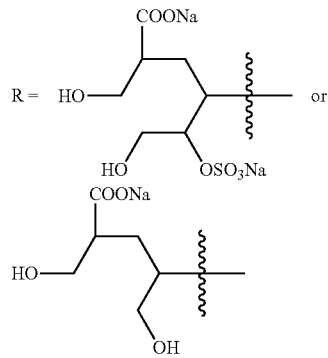

X = H, SO$_3$Na
X' = COCH$_3$, SO$_3$Na
n = 6-12 n' = 1-2.

In some embodiments, the M402 preparation is Necuparinol.

The pharmaceutical compositions described herein can have a shelf life of at least 30 days, e.g., at least two months, at least three months, at least six months, at least nine months, twelve months, or at least eighteen months).

Any preparation or preparation described herein can be manufactured using good manufacturing practices (GMP) as defined by the U.S. Food and Drug Administration (21 CFR Part 110).

Anti-IIa Activity

LMWH preparations are disclosed herein that provide substantially reduced anti-IIa activity, e.g., anti-IIa activity of about less than about 50 IU/mg, less than about 40 IU/mg, 30 IU/mg, 20 IU/mg, 15 IU/mg, 10 IU/mg, 5 IU/mg, 4 IU/mg, 3 IU/mg, 2 IU/mg, 1 IU/mg or less; or from about 0 to 50 IU/mg, about 0 to 40 IU/mg, about 0 to 30 IU/mg, about 0 to 25 IU/mg, about 0 to 20 IU/mg, about 0 to 10 IU/mg, about 0 to 5 IU/mg, about 5 to 10 IU/mg, about 5 to 15 IU/mg, or about 5 to 20 IU/mg). Anti-IIa activity is calculated in International Units of anti-IIa activity per milligram using statistical methods for parallel line assays. The anti-IIa activity levels described herein are measured using the following principle.

Polysaccharide (PS)+ATIII→[PS•ATIII]IIa

PS•ATIII→[PS•ATIII•IIa]+IIa (Excess)

IIa (Excess)+Substrate→Peptide+pNA (measured spectrophotometrically)

Anti-factor IIa activity is determined by the sample potentiating effect on antithrombin (ATIII) in the inhibition of thrombin. Thrombin excess can be indirectly spectrophotometrically measured. The anti-factor IIa activity can be measured, e.g., on a Diagnostica Stago analyzer or on an ACL Futura3 Coagulation system, with reagents from Chromogenix (S-2238 substrate, Thrombin (53 nkat/vial), and Antithrombin), or on any equivalent system. Analyzer response is calibrated using the 2nd International Standard for Low Molecular Weight Heparin.

Anti-Xa Activity

In some embodiments, a LMWH preparation provided herein has anti-Xa activity of less than about 50 IU/mg, less than about 40 IU/mg, 30 IU/mg, 20 IU/mg, 15 IU/mg, 10 IU/mg, 5 IU/mg, 4 IU/mg, 3 IU/mg, 2 IU/mg, 1 IU/mg or less, or about 0 to 50 IU/mg, e.g., 50 IU/mg, 40 IU/mg, 30 IU/mg, 20 IU/mg, 15 IU/mg, 10 IU/mg, 5 IU/mg, 4 IU/mg, 3 IU/mg, 2 IU/mg or 1 IU/mg; or from about 0 to 50 IU/mg, about 0 to 40 IU/mg, about 0 to 30 IU/mg, about 0 to 25 IU/mg, about 0 to 20 IU/mg, about 0 to 10 IU/mg, about 0 to 5 IU/mg, about 5 to 10 IU/mg, about 5 to 15 IU/mg, or about 5 to 20 IU/mg). In some embodiments, a LMWH preparation provided herein has anti-Xa activity of about 2 IU/mg. Anti-Xa activity of a preparation is calculated in International Units of anti-factor Xa activity per milligram using statistical methods for parallel line assays. The anti-factor Xa activity of preparations described herein is measured using the following principle:

PS+ATIII→[PS•ATIII]FXa

PS•ATIII→[PS•ATIII•FXa]+FXa(Excess)

FXa (Excess)+Substrate→Peptide+pNA (measured spectrophotometrically)

The anti-factor Xa activity is determined by the sample potentiating effect on antithrombin (ATIII) in the inhibition of activated Factor Xa (FXa). Factor Xa excess can be indirectly spectrophotometrically measured. Anti-factor Xa activity can be measured, e.g., on a Diagnostica Stago analyzer with the Stachrom® Heparin Test kit, on an ACL Futura3 Coagulation system with the Coatest® Heparin Kit from Chromogenix, or on any equivalent system. Analyzer response can be calibrated using the NIBSC International Standard for Low Molecular Weight Heparin.

Molecular Weight and Chain Length

LMWH preparations included in the pharmaceutical compositions can have a weight average molecular weight described herein.

"Weight average molecular weight" as used herein refers to the weight average in daltons of chains of uronic acid/hexosamine disaccharide repeats. The weight average molecular weight ($M_w$) is calculated from the following equation: $M_w=\Sigma(c_i m_i)/\Sigma c_i$. The variable $c_i$ is the concentration of the polymer in slice i and $m_i$ is the molecular weight of the polymer in slice i. The summations are taken over a chromatographic peak, which contains many slices of data. A slice of data can be pictured as a vertical line on a plot of chromatographic peak versus time. The elution peak can therefore be divided into many slices. The weight average molecular weight calculation is average dependant on the summation of all slices of the concentration and molecular weight. The weight average molar weight can be measured, e.g., using the Wyatt Astra software or any appropriate software. The weight average molecular weights described herein are determined by high liquid chromatography with two columns in series, for example a TSK G3000 SWXL and a G2000 SWXL, coupled with a UV or multi angle light scattering (MALS) detector and a refractometric detector in series. The eluent used is a 0.2 M sodium sulfate, pH 5.0, and a flow rate of 0.5 mL/min.

A determination of whether a LMWH preparation includes chains of sufficient chain length can be made, for example, by determining the average chain length of the chains in the preparation and/or by determining the weight average molecular weight of chains within the preparation. For example, when weight average molecular weight of a preparation is determined, a weight average molecular weight of about 3500 to 8000 Da, about 4000 to 8000 Da, about 4200 to 8000, or about 4500 to 8000 Da, indicates that a significant number of chains in the LMWH preparation are of a chain length described herein, e.g., for M402, n+n' has an average chain length of 7 to 14.

"Average chain length" as used herein refers to the average chain length of uronic acid/hexosamine disaccharide repeats that occur within a chain. Average chain length is determined by dividing the number average molecular weight (Mn) by the number average molecular weight for a disaccharide (500 Da).

Molecular Weight Distribution

The molecular weight distribution of a LMWH preparation described herein can be determined by known methods.

In some embodiments, a LMWH preparation described herein has a molecular weight distribution such that 10-50% (e.g., 10-40%, 10-30%, 15-30% or 15-25%) of the oligosaccharides of the preparation have a molecular weight <3000 Da; 40-65% (e.g., 40-60%, 45-65%, 50-65%, or 55-65%) of the oligosaccharides have a molecular weight between 3000-8000 Da, and 5-30% (e.g., 10-30%, 15-30%, 10-25%, or 15-25%) of the oligosaccharides have a molecular weight >8000 Da. In certain embodiments, a LMWH preparation described herein has a molecular weight distribution such that 10-40% of the oligosaccharides of the preparation have a molecular weight <3000 Da; 45-65% of the oligosaccharides have a molecular weight between 3000-8000 Da, and 15-30% of the oligosaccharides have a molecular weight >8000 Da.

Glycol Split Uronic Acids

A LMWH preparation described herein can include an opening of the glycoside ring, conventionally called reduction-oxidation (RO) derivatives. In these preparations, one or more glycoside rings having vicinyl diols that are opened, e.g., at the bond between C2 and C3, by means of an oxidation action, followed by a reduction. The compounds referred to herein will also be called "Glycol Split" derivatives.

In a further embodiment of the invention described herein, the glycol split residues lend themselves to the subsequent functionalization. Therefore, the compounds may also bear equal or different groups, in place of the primary hydroxy groups deriving from glycol split, for example, aldehyde groups, methoxy groups, or oligosaccharide or peptide groups, ranging from a single saccharide or amino acid to more than one unit of length, e.g., 2 or 3 units.

In some embodiments, fewer than 50% of the uronic acid residues are glycol split uronic acid residues (e.g., less than 40%, 30%, 25%, or 20% of the uronic acid residues are glycol split uronic acid residues).

Reducing End Structures

In some instances, at least about 50% of the chains in a LMWH preparation described herein have a modified reducing end structure such as a 2,5-anhydromannose residue or a 2,5-anhydromannose that has been reduced to form an alcohol. In some embodiments, at least about 55%, 60%, 65%, 70%, 75%, 80%, 85%, 90%, or 95% of the chains in the preparation have a modified reducing end structure, such that the reducing end includes a 2,5-anhydromannose residue or a 2,5-anhydromannitol.

Non-Reducing End Structures

In some embodiments, at least about 55%, 60%, 65%, 70%, 75%, 80%, 85%, 90%, 95%, or 100% of the chains of a LMWH preparation described herein have a uronic acid at the non-reducing end. In some embodiments, at least about 55%, 60%, 65%, 70%, 75%, 80%, 85%, 90%, 95%, or 100% of the chains of a LMWH preparation described herein have a non native uronic acid at the non-reducing end. In some embodiments, at least about 55%, 60%, 65%, 70%, 75%, 80%, 85%, 90%, 95%, or 100% of the chains of a LMWH preparation described herein have a glycol split uronic acid at the non-reducing end. In some embodiments, the non reducing end of chains of the LMWH preparation has one or more the following structure:
is

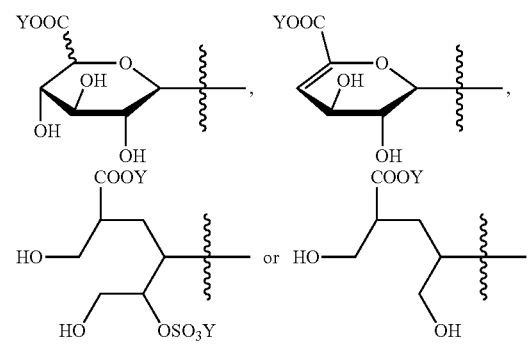

wherein each Y is independently a singularly charged cation such as $Na^+$, $K^+$, or $NH_4^+$.

In one embodiment, the non-reducing end of the chains of the LMWH preparation have the following structures:

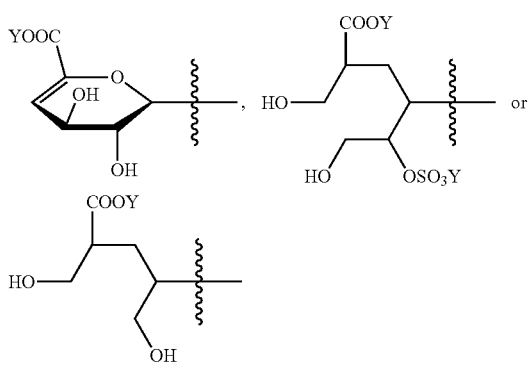

wherein each Y is independently a singularly charged cation such as $Na^+$, $K^+$, or $NH_4^+$.

In one embodiment, the non-reducing end of the chains of the LMWH preparation have the following structures:

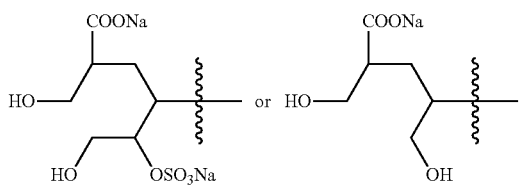

and combinations thereof.

Polydispersity

The polydispersity of LMWH preparations provided herein is about 2 or less, e.g., 1.7 or less, e.g., about 1.9, 1.8, 1.7 or 1.6 to 1.2, about 1.4-1.5, and numbers in between.

The term "polydisperse" or "polydispersity" refers to the weight average molecular weight of a preparation (Mw) divided by the number average molecular weight (Mn). The number average molecular weight (Mn) is calculated from the following equation: $Mn=\Sigma ci/(\Sigma ci/mi)$. The variable ci is the concentration of the polysaccharide in slice i and Mi is the molecular weight of the polysaccharide in slice i. The summations are taken over a chromatographic peak, which contains many slices of data. A slice of data can be pictured as a vertical line on a plot of chromatographic peak versus time. The elution peak can therefore be divided into many slices. The number average molecular weight is a calculation dependent on the molecular weight and concentration at each slice of data. Methods of determining weight average molecular weight are described above, and were used to determine polydispersity as well.

Methods of Making LMWH preparations

The LMWH preparation can be made, e.g., by known methods. In some embodiments, a LMWH preparation lacking substantial anticoagulant activity can be made by a method that includes providing a precursor LMWH preparation having a weight average molecular weight of greater than 7000 Da or a chain length of greater than 7 to 18 disaccharides, and processing the precursor LMWH preparation (e.g., by enzymatic or chemical depolymerization, e.g., by nitrous acid depolymerization) to obtain a LMWH preparation having a weight average molecular weight of about 3000 to 8000 Da or an average chain length of about 7 to 16 disaccharides. For example, the precursor LMWH preparation can be unfractionated heparin.

The precursor LMWH preparation can be processed by a method comprising depolymerization (e.g., by nitrous acid treatment, hydrolysis, or enzymatic depolymerization) followed by a glycol split reaction. Nitrous acid depolymerization can be accomplished, e.g., by treating the precursor LMWH preparation (e.g., UFH) with nitrous acid (e.g., about 0.02 to 0.04 M nitrous acid) at a pH of about 2 to 4 for a specified period of time (e.g., about 1 to 5 hours) at a temperature of about 10 to 30° C. The glycol split reaction involves periodate oxidation using periodate (e.g., about 0.05 M to 0.2 M sodium periodate) for about 10 to 20 hours at a temperature of about 0 to 10° C. In some embodiments, residual impurities such as salts or diethylene glycol (DEG) can be subsequently removed by a chromatographic method, e.g. gel filtration chromatography. Optionally, the oxidized preparation is then reduced by treatment with a reducing agent (e.g., about 0.5 to 2.0% (w/v) sodium borohydride) for about 0.5 to 3 hours at a pH of about 6.0 to 7.0 and a temperature of about 0 to 10° C.

A precursor LMWH preparation can be processed using enzymatic digestion, chemical digestion or combinations thereof. Examples of chemical digestion include oxidative depolymerization, e.g., with $H_2O_2$ or $Cu^+$ and $H_2O_2$, deaminative cleavage, e.g., with isoamyl nitrite or nitrous acid, β-eliminative cleavage, e.g., with benzyl ester, and/or by alkaline treatment. Enzymatic digestion can include the use of one or more heparin degrading enzymes. For example, the heparin degrading enzyme(s) can be, e.g., one or more heparanase, heparin lyase, heparan sulfate glycoaminoglycan (HSGAG) lyase, a lyase described as a glycoaminoglycan (GAG) lyase that can also degrade heparin. In some embodiments, the enzyme cleaves at one or more glycosidic linkages of unsulfated uronic acids.

Other Pharmaceutical Composition Components

The compositions described herein can include additional components, such as one or more of a preservative, surfactant, tonicity agent (e.g., a polyol), bulking agent, buffering agent, or antioxidant.

Buffering Agents

In some embodiments, compositions described herein include one or more, e.g., 1, 2, 3, 4, 5, or more buffering agents.

In some embodiments, the composition includes one or more, e.g., 1, 2, 3, 4, 5, or more buffering agents, and the pH of the composition is between about 5.0-9.0, 5.0-8.0, 5.5-8.0, 6.0-8.0, 6.1-8.0, 6.2-8.0, 6.3-8.0, 6.4-8.0, or 6.5-8.0.

In some embodiments, the composition includes one or more, e.g., 1, 2, 3, 4, 5, or more buffering agents, and the pH of the composition is about 6.0 or above, 6.1 or above, 6.2 or above, 6.3 or above, 6.4 or above, or 6.5 or above.

In some embodiments, the composition includes one or more, e.g., 1, 2, 3, 4, 5, or more buffering agents, and the pH of the composition is about 6.1. In some embodiments, the composition includes one or more, e.g., 1, 2, 3, 4, 5, or more buffering agents and the pH of the composition is about 6.2. In some embodiments, the composition includes one or more, e.g., 1, 2, 3, 4, 5, or more buffering agents, and the pH of the composition is about 6.3. In some embodiments, the composition includes one or more, e.g., 1, 2, 3, 4, 5, or more buffering agents, and the pH of the composition is about 6.4. In some embodiments, the composition includes one or more, e.g., 1, 2, 3, 4, 5, or more buffering agents, and the pH of the composition is about 6.5. In some embodiments, the composition includes one or more, e.g., 1, 2, 3, 4, 5, or more buffering agents, and the pH of the composition is about 6.6.

In some embodiments, the composition includes one or more buffering agents with at least one (e.g., 1, 2, 3, or more) pKa between about 4.0-9.0. In some embodiments, the composition includes one or more buffering agents with a pKa between about 3.0-10.0. In some embodiments, the composition includes one or more buffering agents with a pKa between about 5.0-9.0. In some embodiments, the composition includes one or more buffering agents with a pKa between about 5.0-7.0. In some embodiments, the composition includes one or more buffering agents with a pKa between about 5.0-6.0. In some embodiments, the composition includes one or more buffering agents with a pKa between about 4.0-8.0. In some embodiments, the composition includes one or more buffering agents with a pKa between about 4.0-7.0. In some embodiments, the composition includes one or more buffering agents with a pKa between about 4.0-6.0. In some embodiments, the composition includes one or more buffering agents with a pKa between about 4.0-5.0.

In some embodiments, where multiple buffering agents are present, the pKa of each buffering agent is distinct. In some embodiments, where multiple buffering agents are present, the pKa of the buffering agents is overlapping. In some embodiments, where multiple buffering agents are present, the pKa of the buffering agents is distinct or overlapping such that one or more buffering agents are buffering at a predetermined time and/or pH and/or such that one or more buffering agents can serve as a buffer across a pH range described herein.

In some embodiments, compositions described herein have a pH that is less than the pKa of a buffering agent present in the composition. In some embodiments, compositions described herein have a pH that is equal to the pKa of a buffering agent present in the composition. In some embodiments, compositions described herein have a pH that is greater than the pKa of a buffering agent present in the composition. The relationship between the pH of the composition and the pKa of a buffer in the composition can be predetermined, e.g., wherein the pH is less than, equal to, or greater than, a buffering agent present in the composition. In some embodiments, the pH of the composition can be about 0.001, about 0.001, about 0.01, about 0.1, about 0.5, about 1.0, about 1.5, about 2.0, about 2.5, about 3.0, about 3.5, about 4.0, about 4.5, about 5.0, about 5.5, about 6.0 or more units greater than the pKa of a buffer in the composition.

In some embodiments, compositions described herein include one or more buffering agent, including but not limited to: a citrate buffer, a phosphate buffer, a histidine buffer, a maleate buffer, a succinate buffer, an acetate buffer, a malate buffer, or any combination thereof. In some embodiments, compositions described herein include one or more buffering agent, including but not limited to: a citrate buffer, a phosphate buffer, a histidine buffer, a maleate buffer, a succinate buffer, an acetate buffer, a malate buffer. In an embodiment, compositions described herein include a citrate buffer. In some embodiments, compositions described herein include a sodium citrate buffer, e.g., 5-50 mM sodium citrate, e.g., 5-20 mM sodium citrate, e.g., 10 mM sodium citrate. In some embodiments, compositions described herein include a phosphate citrate buffer.

In some embodiments, compositions described herein include a citrate buffer and one or more of a different citrate buffer a phosphate buffer, a histidine buffer, a succinate buffer, an acetate buffer, or a malate buffer. In some embodiments, compositions described herein include a phosphate buffer and one or more of a different phosphate buffer, a citrate buffer, a histidine buffer, a succinate buffer, an acetate buffer, or a malate buffer. In some embodiments, compositions described herein include a histidine buffer and one or more of a different histidine buffer, a phosphate buffer, a citrate buffer, a succinate buffer, an acetate buffer, or a malate buffer. In some embodiments, compositions described herein include a maleate buffer and one or more of a different maleate buffer, a phosphate buffer, a histidine buffer, a citrate buffer, a succinate buffer, or an acetate buffer. In some embodiments, compositions described herein include a succinate buffer and one or more of a different succinate buffer, a phosphate buffer, a histidine buffer, a citrate buffer, an acetate buffer, or a malate buffer. In some embodiments, compositions described herein include an acetate buffer and one or more of a different acetate buffer, a phosphate buffer, a histidine buffer, a citrate buffer, a succinate buffer, or a malate buffer.

pH

In some embodiments, a composition described herein includes a LMWH preparation formulated at a pH, e.g., a buffered pH, which maintains the stability of the polysaccharide chains. In some embodiments, the composition is formulated at a pH, e.g., a buffered pH, that results in a composition that is substantially free of formic acid and/or $C_2H_6O_3$. pH can be determined using standard methods, e.g., methods described herein.

In some embodiments, a composition described herein includes a LMWH preparation formulated at a pH, e.g., a buffered pH, which minimizes degradation of the polysaccharide chains at a predefined temperature, e.g., at about 2-8° c., e.g., 4° C.

In some embodiments, a composition described herein includes a LMWH preparation formulated at a pH, e.g., a buffered pH, which minimizes degradation of the LMWH preparation at a predefined temperature, for a predetermined time, e.g., days, weeks, months, years. In some embodiments, a composition described herein includes a LMWH preparation formulated at a pH, e.g., a buffered pH, which minimizes degradation of the LMWH preparation at a predefined temperature, for a predetermined time, e.g., 1-3 months, 3-6 months, 6-9 months, 9-12 months, 1-12 months, 1-24 months, 1-36 months, 1-6 months, 1-9 months. In some embodiments, a composition described herein includes a LMWH preparation formulated at a pH, e.g., a buffered pH, which minimizes degradation of the LMWH preparation at a predefined temperature, for a predetermined time, e.g., up to 3 months, up to 6 months, up to 9 months, up to 12 months, up to 24 months, up to 36 months. In some embodiments, a composition described herein includes a LMWH preparation formulated at a pH, e.g., a buffered pH, which minimizes degradation of the LMWH preparation at a predefined temperature, for a predetermined time, e.g., at least 3 months, at least 6 months, at least 9 months, at least 12 months, at least 24 months, at least 36 months.

In some embodiments, a composition described herein has a pH between about 4.0-9.0 or above. In some embodiments, the composition has a pH between about 5.0-9.0, 5.0-8.0, 5.5-8.0, 6.0-8.0, 6.1-8.0, 6.2-8.0, 6.3-8.0, 6.4-8.0, or 6.5-8.0. In some embodiments, the composition has a pH of about 6.0 or above, 6.1 or above, 6.2 or above, 6.3 or above, 6.4 or above, or 6.5 or above. In some embodiments, the composition has a pH of about 6.2. In some embodiments, the composition has a pH of about 5.0 or above, 6.0 or above, 7.0 or above, 8.0 or above, 9.0 or above, or 10.0 or above.

Preservative

In some embodiments, compositions described herein include one or more preservatives, e.g., one or more alcohols. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride.

In some embodiments, compositions described herein include one or more alcohols as a preservative. In some embodiments, compositions described herein include one or more alcohols, e.g., an alcohol that functions to maintain sterility. Thus, additional exemplary preservatives include aromatic alcohols such as phenol, phenolic compounds, bisphenol, butyl and benzyl alcohol, allyl parabens such as methyl or propyl paraben, catechol, resorcinol, cyclohexanol, 3-pentanol, and m-cresol. In some embodiments, the preservative is benzyl alcohol. Other suitable alcohols can include, but are not limited to ethanol, polyethylene glycol, chlorobutanol, hydroxybenzoate, and/or phenylethyl alcohol.

In some embodiments, compositions described herein contain an alcohol, e.g., benzyl alcohol, e.g., 1-50 mg/mL, 1-25 mg/mL, 5-50 mg/mL, 5-25 mg/mL, 1-20 mg/mL, 1-15 mg/mL, 10-50 mg/mL, 10-25 mg/mL, 10-15 mg/mL, or 10-20 mg/mL. In an embodiment, compositions described herein contain benzyl alcohol, e.g., 1 mg/mL, 5 mg/mL, 10 mg/mL, 15 mg/mL, 20 mg/mL, 25 mg/mL, 30 mg/mL, 40 mg/mL, or 50 mg/mL. In an embodiment, compositions described herein contain about 15 mg/mL benzyl alcohol.

Antioxidants

In some embodiments, compositions described herein include one or more antioxidants. In some embodiments, compositions described herein include one or more antioxidants that function to reduce oxidation of a species within chains of the LMWH preparation, e.g., aldehydes, of the composition. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite.

In some embodiments, compositions described herein include one or more antioxidants that function to reduce oxidation of one or more buffers in the composition, e.g., histidine.

Surfactant

In some embodiments, a composition described herein can include a surfactant. Exemplary surfactants include detergents include nonionic detergents such as polysorbates (e.g. polysorbates 20, 80 etc) or poloxamers (e.g. poloxamer 188). In certain embodiments, the composition includes a surfactant which is a polysorbate. In another embodiment, the composition contains polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th edi., 1996). In one embodiment, the composition contains between about 0.1 and about 10 mg/ml of polysorbate 80, or between about 0.5 and about 5 mg/ml (e.g., about 1 mg/ml).

Tonicity Agent

In some embodiments, a composition described herein includes a tonicity agent. An exemplary tonicity agent is a polyol.

Articles of Manufacture

In some embodiments, an article of manufacture is provided which contains a pharmaceutical composition described herein and, optionally, provides instructions for its use. The article of manufacture comprises a container. Suitable containers include, for example, bottles, vials (e.g., single chamber vial, or dual chamber vials), syringes (e.g., a single chamber syringe, or a dual chamber syringes) and test tubes. The container may be formed from a variety of materials such as glass or plastic. The container holds the composition and the label on, or associated with, the container may indicate directions for use. For example, the label may further indicate that the composition is useful or intended for subcutaneous or intravenous administration. The container holding the composition may be a multi-use vial, which allows for repeat administrations (e.g. from 2-6 administrations) of the composition. The article of manufacture can also include other materials desirable from a commercial and user standpoint, including other buffers, diluents, filters, needles, syringes, and package inserts with instructions for use.

In some embodiments, an article of manufacture described herein, can include an anaerobic overlay, e.g., a nitrogen overlay, over the composition. The anaerobic overlay can or cannot include $CO_2$. In some aspects, the disclosure features an article of manufacture that contains a composition described herein. In some embodiments, the article of manufacture can include a container, e.g., a container described herein, that includes a pharmaceutical composition described herein. In some embodiments, the container can further include an anaerobic overlay, e.g., a nitrogen overlay. In some embodiments, anaerobic (or minimal oxygen) conditions can be used to maintain the stability of the glycol split LMWH, e.g., under low certain pH conditions (e.g., low pH conditions, e.g, less than pH 6.0). In some instances, anaerobic conditions can be created by replacing air in the headspace of a vial containing liquid M402. Exemplary agents that can be used to replace air include, but are not limited to, nitrogen, an inert gas, e.g., argon. In some embodiments, an anaerobic overlay does not include $CO_2$. In some embodiments, an anaerobic overlay can include $CO_2$. In some instances, Nitrogen (N2) can be used to assess the impact of headspace gas on stability of the LMWH preparation. The N2 overlay can for example, be prepared by placing empty glass vials in a box with an N2 environment (99.99% purity N2), purging air from the vials with N2, and adding prepared preparations to the vials. In some embodiments, a glove box can be purged with N2 gas, maintaining positive pressure and a % RH of less than 10%. For each preparation, empty vials can be placed in the glove box, and using a secondary N2 source with tubing, N2 dispensed into each vial to displace air by holding the tubing over each vial for 4-5 seconds.

Uses

The pharmaceutical compositions described herein can be used to treat a subject.

As used herein, a subject is a mammal, e.g., a non-human experimental mammal, a veterinary mammal, or a human. Non-human mammals include a primate, cow, horse, pig, sheep, goat, dog, cat, or rodent.

The preparations provided herein can be used, for example, to treat or prevent a cancer (e.g., a cancer, e.g., a carcinoma or other solid or hematological cancer, a cancer metastases). As used herein, the term "cancer" is meant to include all types of cancerous growths or oncogenic processes, metastatic tissues or malignantly transformed cells, tissues, or organs, irrespective of histopathologic type or stage of invasiveness. Methods and compositions disclosed herein are particularly useful for treating, or reducing the size, numbers, or rate of growth of, metastatic lesions associated with cancer.

Examples of cancers include, but are not limited to, solid tumors, soft tissue tumors, hematopoietic tumors and metastatic lesions. Examples of solid tumors include malignancies, e.g., sarcomas, adenocarcinomas, and carcinomas, of the various organ systems, such as those affecting head and neck (including pharynx), thyroid, lung (small cell or non small cell lung carcinoma), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neorublastoma or glioma), skin (e.g., melanoma). Examples of hematopoietic cancers that can be treated include hemangiomas, multiple myeloma, lymphomas and leukemias and myelodysplasia. Methods and compositions disclosed herein are particularly useful for treating, e.g., reducing or delaying, metastatic lesions associated with the aforementioned cancers. In some embodiments, the patient will have undergone one or more of surgical removal of a tissue, chemotherapy, or other anti-cancer therapy and the primary or sole target will be metastatic lesions, e.g., metastases in the bone or lymph nodes or lung or liver or peritoneal cavity or the CNS or other organs.

The methods of the invention, e.g., methods of treatment, can further include the step of monitoring the subject, e.g., for a change (e.g., an increase or decrease) in one or more of: tumor size; levels of a cancer marker, for a patient with cancer; the size or rate of appearance of new lesions, e.g., in a scan; the appearance of new disease-related symptoms; the size of soft tissue mass, e.g., a decrease or stabilization; changes in blood flow measured by imaging technology; survival; progression-free survival; quality of life, e.g., amount of disease associated pain, e.g., bone pain; or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same composition or for additional treatment with additional agents. Generally, a decrease in one or more of the parameters described above is indicative of the improved condition of the subject.

The compositions described herein can be administered to a subject in single or multiple doses to treat or prevent a metastatic or cancerous disorder, e.g., a cancerous disorder described herein.

The compositions described herein can also be used to treat inflammatory, autoimmune, fibrotic, fibroproliferative, atopic, or angiogenic disorders. Examples of inflammatory disorders include but are not limited to chronic obstructive pulmonary disease, asthma, rheumatoid arthritis, inflammatory bowel disease (including Crohns disease and ulcerative colitis), multiple sclerosis, psoriasis, ischemia-reperfusion injuries, septic shock, age-related macular degeneration (e.g., wet age-related macular degeneration), atherosclerosis, Alzheimer's disease, Parkinson's disease, cardiovascular disease, vasculitis, type I and II diabetes, metabolic syndrome, diabetic retinopathy, restenosis. Examples of autoimmune diseases include but are not limited to asthma, rheumatoid arthritis, inflammatory bowel disease, multiple sclerosis, psoriasis, type I diabetes, systemic lupus erythematosus (SLE), Sjögren's syndrome, Hashimoto's thyroiditis, Graves' disease, Guillain-Barré syndrome, autoimmune hepatitis, Myasthenia gravis. Examples of fibrotic diseases include but are not limited to scleroderma, liver fibrosis, pancreatic fibrosis, chronic obstructive pulmonary disease, diabetic nephropathy, sarcoidosis, idiopathic pulmonary fibrosis, cirrhosis, cystic fibrosis, neurofibromatosis, endometriosis, post-operative fibroids, restenosis. Examples of atopic disease include but are not limited to atopic dermatitis, atopic asthma, and allergic rhinitis.

Examples of fibroproliferative disorders include systemic and local scleroderma, keloids and hypertrophic scars, atherosclerosis, restenosis, fibrosarcoma, neurofibromatosis, and rheumatoid arthritis. Examples of scarring associated with trauma include scarring due to surgery, chemotherapeutic-induced fibrosis, radiation-induced fibrosis, scarring associated with injury or burns.

In one embodiment, the pharmaceutical compositions are used for inhibiting angiogenesis, e.g., to treat angiogenic disorders. Angiogenesis as used herein is the inappropriate formation of new blood vessels. Angiogenic disorders include, but are not limited to, tumors, neovascular disorders of the eye, endometriosis, macular degeneration, osteoporosis, psoriasis, arthritis, cancer, hemangiomas, and cardiovascular disorders.

It is understood that some disorders will fall within more than one category of disease described herein.

The compositions described herein can also be used to treat or prevent infectious disorders such as, e.g., malaria.

The pharmaceutical composition can be administered to a subject in need of treatment with the therapeutic agent, such as a human, in accord with known methods, such as intravenous administration as a bolus or by continuous infusion over a period of time, by intramuscular, intraperitoneal, intracerebrospinal, subcutaneous, intra-articular, intrasynovial, and intrathecal routes. In an embodiment, the pharmaceutical composition is administered to the subject by subcutaneous (i.e. beneath the skin) administration. For such purposes, the composition may be injected using a syringe. However, other devices for administration of the composition are available such as injection devices (e.g. the Inject-ease™ and Genject™ devices); injector pens (such as the GenPen™); needleless devices (e.g. MediJector™ and BioJector™); and subcutaneous patch delivery systems. In some embodiments, the pharmaceutical composition is administered to the subject by intravenous administration, e.g., as a bolus or by continuous infusion over a period of time.

The appropriate dosage ("therapeutically effective amount") of the therapeutic agent will depend, for example, on the condition to be treated, the severity and course of the condition, whether the therapeutic agent is administered for preventive or therapeutic purposes, previous therapy, the patient's clinical history and response to the protein, the type of therapeutic agent used, and the discretion of the attending physician. The therapeutic agent is suitably administered to the patient at one time or over a series of treatments and may be administered to the patient at any time from diagnosis onwards. The therapeutic agent may be administered as the sole treatment or in conjunction with other drugs or therapies useful in treating the condition in question.

Also described herein is an article of manufacture. An article of manufacture can include a pharmaceutical composition described herein and, e.g., instructions for its use. The article of manufacture comprises a container. Suitable containers include, for example, bottles, vials (e.g. single chamber vials, or dual chamber vials), syringes (such as single chamber syringes, or dual chamber syringes) and test tubes. The container may be formed from a variety of materials such as glass or plastic. The container holds the composition and the label on, or associated with, the container may indicate directions for use. For example, the label may indicate that the composition is useful or intended for subcutaneous or intravenous administration. The container holding the composition may be a multi-use vial, which allows for repeat administrations (e.g. from 2-6 administrations) of the composition. The article of manufacture can also include other materials desirable from a commercial and user standpoint, including other buffers, diluents, filters, needles, syringes, and package inserts with instructions for use.

Combination Therapy

The methods and compositions described herein can be used in combination with other therapeutic modalities. Administered "in combination", as used herein, means that two (or more) different treatments are delivered to the subject during the course of the subject's affliction with the disorder, such that the effects of the treatments on the patient overlap at a point in time. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In one embodiment, the methods of the invention include administering to the subject a composition described herein, in combination with one or more additional therapies, e.g., surgery, radiation therapy, or administration of another therapeutic preparation. In one embodiment, the additional therapy may include chemotherapy, e.g., a cytotoxic agent. In one embodiment the additional therapy may include a targeted therapy, e.g. a tyrosine kinase inhibitor, a proteasome inhibitor, a protease inhibitor. In one embodiment, the additional therapy may include an anti-inflammatory, anti-angiogenic, anti-fibrotic, or anti-proliferative compound, e.g., a steroid, a biologic immunomodulator, a monoclonal antibody, an antibody fragment, an aptamer, an siRNA, an antisense molecule, a fusion protein, a cytokine, a cytokine receptor, a bronchodialator, a statin, an anti-inflammatory agent (e.g. methotrexate), an NSAID. In another embodiment, the additional therapy could include combining therapeutics of different classes. The pharmaceutical composition and the additional therapy can be administered simultaneously or sequentially.

Exemplary cytotoxic agents that can be administered in combination with the pharmaceutical composition include antimicrotubule agents, topoisomerase inhibitors, antimetabolites, protein synthesis and degradation inhibitors, mitotic inhibitors, alkylating agents, platinating agents, inhibitors of nucleic acid synthesis, histone deacetylase and DNA methyltransferase inhibitors, nitrogen mustards, nitrosoureas, ethylenimines, alkyl sulfonates, triazenes, folate analogs, nucleoside analogs, ribnucleotide reductase inhibitors, vinca alkaloids, taxanes, epothilones, intercalating agents, agents capable of interfering with a signal transduction pathway, agents that promote apoptosis and radiation, antibody conjugates that bind surface proteins to deliver a toxic agent. In one embodiment, the cytotoxic agent that can be administered with a composition described herein is a platinum-based agent (such as cisplatin), cyclophosphamide, dacarbazine, methotrexate, fluorouracil, gemcitabine, capecitabine, hydroxyurea, topotecan, irinotecan, azacytidine, vorinostat, ixabepilone, bortezomib, taxanes (paclitaxel, docetaxel), cytochalasin B, gramicidin D, ethidium bromide, emetine, mitomycin, etoposide, tenoposide, vincristine, vinblastine, vinorelbine, colchicin, anthracyclines (doxorubicin and epirubicin) daunorubicin, dihydroxy anthracin dione, mitoxantrone, mithramycin, actinomycin D, adriamycin, 1-dehydrotestosterone, glucocorticoids, procaine, tetracaine, lidocaine, propranolol, puromycin, ricin, and maytansinoids.

In one embodiment, the pharmaceutical composition is administered to treat pancreatic cancer, and the cytotoxic agent can be gemicitabine.

The combination therapy can also include a composition described herein coformulated with, and/or coadministered with, one or more additional therapeutic agents, e.g., one or more anti-cancer agents, cytotoxic or cytostatic agents, hormone treatment, small molecule inhibitors of receptor tyrosine kinases and other tyrosine kinases including HER-2, EGFR, VEGFR, BCR-ABL, c-KIT (such as Gefitinib, Erlotinib, Lapatinib, Sorafenib, Sunitinib, Imatinib, Dasatinib, Nilotinib) or mTOR (such as temsirolimus, everolimus, rapamycin), or cytokines or chemokines, vaccines, antibodies against cell membrane receptors pathways including EGF-EGFR, VEGF-VEGFR, CD19, CD20, CD3, CTLA-4 (such as Trastuzumab, Cetuximab, Panitumumab, Bevacizumab, Rituximab, Tositumomab) and/or other immunotherapies.

Anti-angiogenic Agent or Tyrosine Kinase Inhibitors

The pharmaceutical composition described herein can be administered in combination with an anti-angiogenic agent or tyrosine kinase inhibitor to treat a subject having cancer, e.g., a primary tumor, or having or at risk of having metastasis of a primary tumor.

In one embodiment, the anti-angiogenic agent or tyrosine kinase inhibitor is administered in an amount and/or dosing schedule that is associated with (e.g., causes) bone marrow derived progenitor cell mobilization. For example, the anti-angiogenic agent or tyrosine kinase inhibitor is administered in an amount and/or dosing schedule that is associated with (e.g., causes) endothelial progenitor cell mobilization.

In one embodiment, the anti-angiogenic agent or tyrosine kinase inhibitor selected from the group consisting of: an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a TGF pathway inhibitor, a KIT pathway inhibitor, a RAF-1 inhibitor and a RET inhibitor. In some embodiments, the subject has been treated or will be treated with an anti-angiogenic agent or a tyrosine kinase inhibitor selected from the group consisting of: bevacizumab (Avastin®), ranibizumab (Lucentis®), imatinib (Gleevec®), cetuximab (Erbitux®), sunitinib (Sutent®), sorafenib (Nexavar®), tivozanib (AV-951), cediranib (AZD2171), dasatinib (Sprycel®), nilotinib (AMN-107), CP-547632, erlotinib (Tarceva®), panitumumab (Vectibix®), pazopanib (Votrient®), axitinib and gefitinib (Iressa®).

A PDGF pathway inhibitor includes, without limitation, tyrphostin AG 1296, tyrphostin 9,1,3-butadiene-1,1,3-tricarbonitrile, 2-amino-4-(1H-indol-5-yl)-(9Cl), imatinib (Gleevec®) and gefitinib (Iressa®) and those compounds generically and specifically disclosed in European Patent No.: 0 564 409 and PCT Publication No.: WO 99/03854.

A VEGF pathway inhibitor includes, without limitation, anti-VEGF antibodies, e.g., bevacizumab (Avastin®), and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™).

A EGF pathway inhibitor includes, without limitation, anti-EGFR antibodies, e.g., cetuximab (Erbitux®), panitumumab (Vectibix®), and gefitinib (Iressa®), and small molecules such as tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980.

In one embodiment, the cancer is gastrointestinal cancer. The gastrointestinal cancer can be a chemotherapeutic refractory, a chemotherapeutic resistant, and/or a relapsed cancer, e.g., the gastrointestinal cancer is refractory to imatinib mesylate, resistant to imatinib mesylate or relapsed after treatment with imatinib mesylate.

In an embodiment, the cancer is renal cell cancer, e.g., advanced or metastatic renal cell carcinoma, e.g., a chemotherapeutic refractory, a chemotherapeutic resistant, and/or a relapsed carcinoma, e.g., the renal cell carcinoma is refractory to a cytokine (e.g., interleukin-2 or interferon), resistant to a cytokine (e.g., interleukin-2 or interferon) or relapsed after treatment with a cytokine (e.g., interleukin-2 or interferon). In some embodiments, a renal cell cancer is treated with pazopanib (Votrient®) (e.g., at a dose of 800 mg or less (e.g., 600 mg, 400 mg, 200 mg) daily, or sorafenib (Nexavar®) in combination with a pharmaceutical composition described herein.

In an embodiment, the cancer is colorectal cancer, e.g., metastatic colorectal cancer, e.g., a chemotherapeutic refractory, a chemotherapeutic resistant, and/or a relapsed cancer. In some embodiments, a colorectal cell cancer is treated with a pharmaceutical composition described herein in combination with bevacizumab (Avastin®) (e.g., at a dose of 5 to 10 mg/kg every 12, 13, 14, 15, 16 days), e.g., in further combination with one or more of a topoisomerase inhibitor (e.g., topotecan, irinotecan, etoposide, teniposide, lamellarin D, camptothecin), a platinum-based agent (e.g., cisplatin, carboplatin, oxaliplatin), an antimetabolite (e.g., 5FU) and leucovorin.

In an embodiment, the cancer is lung cancer, e.g., non-small cell lung cancer, e.g., a chemotherapeutic refractory, a chemotherapeutic resistant, and/or a relapsed cancer. In some embodiments, the lung cell cancer is treated with a pharmaceutical composition described herein in combination with bevacizumab (Avastin®) (e.g., at a dose of 5 to 10 mg/kg every 12, 13, 14, 15, 16 days), e.g., in further combination with one or more of a topoisomerase inhibitor (e.g., topotecan, irinotecan, etoposide, teniposide, lamellarin D, camptothecin), a platinum-based agent (e.g., cisplatin, carboplatin, oxaliplatin), an antimetabolite (e.g., 5FU) and leucovorin.

In an embodiment, the cancer is breast cancer, e.g., metastatic breast cancer, e.g., a chemotherapeutic refractory, a chemotherapeutic resistant, and/or a relapsed breast cancer. In some embodiments, the breast cancer is treated with a pharmaceutical composition described herein in combination with bevacizumab (Avastin®) (e.g., at a dose of 5 to 10 mg/kg every 12, 13, 14, 15, 16 days), e.g., in further combination with a taxane (e.g., docetaxel, paclitaxel). Also, e.g., in combination with anthracycline (daunorubicin (Daunomycin®), Doxorubicin (Adriamycin®)), e.g. in combination with platinum (e.g. cisplatin) e.g., in combination with estrogen inhibitor (e.g. aromatase inhibitors, tamoxifen (Nolvadex®), exemestane (Aromasin®), anastrozole (Arimidex®) and letrozole (Femara®), e.g. in combination with EGF/HER2 inhibitors (e.g. Lapatinib (Tykerb®), trastuzumab (Herceptin®).

In an embodiment, the cancer is a glioblastoma, e.g., a chemotherapeutic refractory, a chemotherapeutic resistant, and/or a relapsed glioblastoma. In certain embodiments, the glioblastoma is treated with a pharmaceutical composition described herein in combination with bevacizumab (Avastin®) (e.g., at a dose of 5 to 10 mg/kg every 12, 13, 14, 15, 16 days).

In one embodiment, the cancer is gastrointestinal cancer and a pharmaceutical composition described herein is administered in combination with 20 mg, 25 mg, 30 mg, 35 mg, 40 mg, 45, mg, 50 mg, 55 mg, 60 mg sunitinib or placebo orally, once daily, on a schedule. In one embodiment, the schedule is administration of sunitinib every day for three, four or five weeks followed by one, two or three weeks of no administration or continuously without 'drug holiday'.

In one embodiment, the cancer is renal cell cancer (e.g., metastatic renal cell cancer). The renal cell cancer can be resistant, relapsed or refractory to treatment with, e.g., a cytokine (e.g., interferon-α, interleukin-2, or a combination thereof). A pharmaceutical composition described herein can be administered in combination with 20 mg, 25 mg, 30 mg, 35 mg, 40 mg, 45 mg, 50 mg, 55 mg, 60 mg sunitinib orally, once daily, on a schedule. In one embodiment, the schedule is administration of sunitinib every day for three, four or five weeks followed by one, two or three weeks of no administration.

In an embodiment, the cancer is a leukemia (e.g., chronic myeloid leukemia or acute lymphoblastic leukemia, e.g., Philadelphia chromosome positive chronic myeloid leukemia or acute lymphoblastic leukemia), e.g., a chemotherapeutic refractory, a chemotherapeutic resistant, and/or a relapsed leukemia, e.g., refractory, a chemotherapeutic resistant, and/or a relapsed to imatinib. In some embodiments, the leukemia is treated with a pharmaceutical composition described herein in combination with dasatinib (e.g., at a dose of 120 mg/day, 130 mg/day, 140 mg/day, 150 mg/day, e.g., administered twice daily).

In an embodiment, the cancer is a pancreatic cancer (e.g., advanced pancreatic cancer). In some embodiments, the pancreatic cancer is treated with a pharmaceutical composition described herein in combination with gemcitabine, Tarceva, Abraxane (a taxol conjugate), a mTOR inhibitors, a VEGF inhibitor (e.g., a VEGF inhibitor described herein), a sonic hedgehog inhibitor.

Vascular Disrupting Agents

The pharmaceutical composition described herein can be administered in combination with a vascular disrupting agent to treat a subject having cancer, e.g., a primary tumor, or having or at risk of having metastasis of a primary tumor. The administration of vascular disrupting agents is associated with mobilization of bone marrow derived progenitor cells such as endothelial progenitor cells in subjects having cancer.

In one embodiment, the vascular disrupting agent is administered in an amount and/or dosing schedule that is associated with (e.g., causes) bone marrow derived progenitor cell mobilization. For example, the vascular disrupting agent is administered in an amount and/or dosing schedule that is associated with (e.g., causes) endothelial progenitor cell mobilization.

Exemplary vascular disrupting agents include, but are not limited to, AVE8062, vadimezan, ZD6126, combretastatin A-4 disodium phosphate (CA4P) or Oxi4503, DMXAA (ASA404), NPI-2358.

In one embodiment, the cancer is lung cancer (e.g., small cell lung cancer or non-small cell lung cancer). The lung cancer can be resistant, relapsed or refractory to treatment with a chemotherapeutic agent, e.g., a VEGF pathway inhibitor (e.g., bevacizumab) or an EGF pathway inhibitor. The lung cancer can be locally advanced or metastatic lung cancer. In another embodiment, the cancer is urothelial cancer (e.g., cancer of the bladder, urethra, ureter, renal pelvis), e.g., locally advanced or metastatic urothelial cancer. The urothelial cancer can be resistant, relapsed or refractory to another chemotherapeutic agent, e.g., a platinum based agent (e.g., cisplatin, carboplatin, oxaliplatin) or a pyrimidine analog (e.g., gemcitabine). A pharmaceutical composition described herein can be administered in combination with ASA404, e.g., ASA404 at a dose of 1,600 mg/m$^2$, 1,700 mg/m$^2$, 1,800 mg/m$^2$, 1,900 mg/m$^2$, 2,000 mg/m$^2$ on a schedule. In one embodiment, the schedule is administration of ASA404 every 18, 19 20, 21, 22, 23 or 24 days, e.g., for 4, 5, 6, 7 cycles. The treatment can further include administration of one or more additional chemotherapeutic agent, e.g., a taxane (e.g., docetaxel, paclitaxel) or a platinum based agent (e.g., cisplatin, carboplatin, oxaliplatin).

In an embodiment, the cancer is lung cancer (e.g., small cell lung cancer or non small cell lung cancer), e.g., metastatic or locally advanced lung cancer, e.g., a chemotherapeutic refractory, a chemotherapeutic resistant, and/or a relapsed lung cancer. In some embodiments, the lung cancer is treated with a pharmaceutical composition described herein in combination with NPI-2358 (e.g., at a dose of 20, 30, 40 mg/m$^2$). In an embodiment, a pharmaceutical composition described herein can be administered in combination with flurouracil/leucovorin.

In an embodiment, the cancer is pancreatic cancer, e.g., metastatic pancreatic cancer. A pharmaceutical composition described herein can be administered in combination with gemcitabine. In one embodiment, the pharmaceutical composition described herein can be administered in combination with gemcitabine and Abraxane (a taxol conjugate).

In an embodiment, the cancer is liver cancer. In an embodiment, a pharmaceutical composition described herein can be administered in combination with flurouracil/leucovorin.

In an embodiment, the cancer is breast cancer. In an embodiment, a pharmaceutical composition described herein can be administered in combination with docetaxel.

In an embodiment, the cancer is a head and neck cancer (e.g., anaplastic carcinoma of the thyroid), e.g., locally advanced or metastatic head and neck cancer. In another embodiment, the cancer is a glioma. In yet another embodiment, the cancer is lung cancer (e.g., small cell lung cancer or non small cell lung cancer), e.g., locally advanced or metastatic lung cancer. The cancer can be chemotherapeutic refractory, a chemotherapeutic resistant, and/or a relapsed. In certain embodiments, the cancer is treated with a pharmaceutical composition described herein in combination with CA4P (e.g., at a dose of 50 mg/m$^2$, 60 mg/m$^2$, 70 mg/m$^2$ on a schedule. The dosing schedule can be, e.g., administration of CA4P weekly for three weeks then one week without administration.

In an embodiment, the cancer is a sarcoma (e.g., a soft tissue sarcoma), e.g., locally advanced or metastatic sarcoma. The cancer can be chemotherapeutic refractory, a chemotherapeutic resistant, and/or a relapsed to another chemotherapeutic agent, e.g., an anthracycline or an alkylating agent (e.g., ifosfamide). In certain embodiments, the cancer is treated with a pharmaceutical composition described herein in combination with AVE8026 (e.g., at a dose of 15 mg/m$^2$, 20 mg/m$^2$, 25 mg/m$^2$, 30 mg/m$^2$ on a schedule). The dosing schedule can be, e.g., administration of AVE8026 every three weeks. In some embodiments, the treatment can further include administration of one or more additional chemotherapeutic agents, e.g., a platinum based agent (e.g., cisplatin, carboplatin, oxaliplatin) and a taxane (e.g., docetaxel, paclitaxel).

Taxanes

The pharmaceutical composition described herein can be administered in combination with a taxane to treat a subject having cancer, e.g., a primary tumor, or having or at risk of having metastasis of a primary tumor. As discussed herein, administration of a taxane to a subject having cancer is associated with mobilization of bone marrow derived progenitor cells such as endothelial progenitor cells.

In one embodiment, the taxane is administered in an amount and/or dosing schedule that is associated with (e.g., causes) bone marrow derived progenitor cell mobilization. For example, the taxane is administered in an amount and/or dosing schedule that is associated with (e.g., causes) endothelial progenitor cell mobilization.

In one embodiment, the cancer is breast cancer (e.g., locally advanced or metastatic breast cancer). The breast cancer can be estrogen receptor positive breast cancer; estrogen receptor negative breast cancer; HER-2 positive breast cancer; HER-2 negative breast cancer; progesterone receptor positive breast cancer; progesterone receptor negative breast cancer; estrogen receptor negative, HER-2 negative and progesterone receptor negative breast cancer (i.e., triple negative breast cancer). The breast cancer can be resistant, relapsed or refractory to treatment with a chemotherapeutic agent, e.g., an alkylating agent (e.g., cyclophosphamide, dacarbazine, melphalan, ifosfamide, temozolomide) or an anthracycline (e.g., daunorubicin, doxorubicin, epirubicin, valrubicin and idarubicin). In some embodiments, a pharmaceutical composition described herein can be administered in combination with docetaxel, e.g., docetaxel at a dose of 60 mg/m$^2$, 70 mg/m$^2$, 75 mg/m$^2$, 80 mg/m$^2$, 90 mg/m$^2$, 100mg/m$^2$, 105 mg/m$^2$, 110 mg/m$^2$, 115 mg/m$^2$ on a schedule. In one embodiment, the schedule is administration of docetaxel every three weeks. In another embodiment, a pharmaceutical composition described herein can be administered in combination with paclitaxel, e.g., paclitaxel at a dose of 125 mg/m$^2$, 135 mg/m$^2$, 145 mg/m$^2$, e.g., infused over about 2, 3, or 4 hours, or 165 mg/m$^2$, 175 mg/m$^2$, 185 mg/m$^2$, 195 mg/m$^2$, e.g., infused over about 22, 23, 24 or 25 hours, on a schedule. In one embodiment, the schedule is administration of paclitaxel every three weeks. The treatment can further include administration of one or more additional chemotherapeutic agent, e.g., a vinca alkaloid (e.g., vinblastine, vincristine, vindesine, vinorelbine) or an anthracycline (e.g., daunorubicin, doxorubicin, epirubicin, valrubicin and idarubicin, or a platinum based agent (e.g. cisplatin).

In another embodiment, the cancer is lung cancer (e.g., small cell lung cancer or non small cell lung cancer), e.g., locally advanced or metastatic lung cancer. The lung cancer can be resistant, relapsed or refractory to another chemotherapeutic agent, e.g., a platinum based agent (e.g., cisplatin, carboplatin, oxaliplatin). A pharmaceutical composition described herein can be administered in combination with docetaxel, e.g., docetaxel at a dose of 60 mg/m$^2$, 70 mg/m$^2$, 75 mg/m$^2$, 80 mg/m$^2$, 90 mg/m$^2$, 100 mg/m$^2$, 105 mg/m$^2$, 110 mg/m$^2$, 115 mg/m$^2$ on a schedule. In one embodiment, the schedule is administration of docetaxel every three weeks. In another embodiment, a pharmaceutical composition described herein can be administered in combination with paclitaxel, e.g., paclitaxel at a dose of 125 mg/m$^2$, 135 mg/m$^2$, 145 mg/m$^2$, e.g., infused over about 2, 3, or 4 hours, or 165 mg/m$^2$, 175 mg/m$^2$, 185 mg/m$^2$, 195 mg/m$^2$, e.g., infused over about 22, 23, 24 or 25 hours, on a schedule. In one embodiment, the schedule is administration of docetaxel every three weeks. The treatment can further include administration of one or more additional chemotherapeutic agent, e.g., a vinca alkaloid (e.g., vinblastine, vincristine, vindesine, vinorelbine) or an alkylating agent (e.g., cyclophosphamide, dacarbazine, melphalan, ifosfamide, temozolomide).

In one embodiment, the cancer is prostate cancer (e.g., locally advanced or metastatic prostate cancer). The prostate cancer can be resistant, relapsed or refractory to treatment with a chemotherapeutic agent. A pharmaceutical composition described herein can be administered in combination with docetaxel, e.g., docetaxel at a dose of 60 mg /m$^2$, 70 mg/m$^2$, 75 mg/m$^2$, 80 mg/m$^2$, 90 mg/m$^2$, 100 mg/m$^2$, 105 mg/m$^2$, 110 mg/m$^2$, 115 mg/m$^2$ on a schedule. In one embodiment, the schedule is administration of docetaxel every three weeks. In another embodiment, a pharmaceutical composition described herein can be administered in combination with docetaxel, e.g., docetaxel at a dose of 20 mg/m$^2$, 25 mg/m$^2$, 30 mg/m$^2$, 35 mg/m$^2$, 40 mg/m$^2$ on a schedule. In one embodiment, the schedule is weekly administration of docetaxel. The treatment can further include administration of one or more additional chemotherapeutic agent.

In one embodiment, the cancer is ovarian cancer (e.g., locally advanced or metastatic ovarian cancer). The ovarian cancer can be resistant, relapsed or refractory to treatment with a chemotherapeutic agent, e.g., a platinum based agent (e.g., cisplatin, carboplatin, oxaliplatin). A pharmaceutical composition described herein can be administered in combination with paclitaxel, e.g., paclitaxel at a dose of 125 mg/m$^2$, 135 mg/m$^2$, 145 mg/m$^2$, e.g., infused over about 2, 3, or 4 hours, or 165 mg/m$^2$, 175 mg/m$^2$, 185 mg/m$^2$, 195 mg/m$^2$, e.g., infused over about 22, 23, 24 or 25 hours, on a schedule. In one embodiment, the schedule is administration of paclitaxel every three weeks. The treatment can further include administration of one or more additional chemotherapeutic agent.

In one embodiment, the cancer is a sarcoma (e.g., AIDS-related Kaposi sarcoma), e.g., locally advanced or metastatic sarcoma). The sarcoma can be resistant, relapsed or refractory to treatment with a chemotherapeutic agent, e.g., an anthracycline (e.g., daunorubicin, doxorubicin, epirubicin, valrubicin and idarubicin). A pharmaceutical composition described herein can be administered in combination with paclitaxel, e.g., paclitaxel at a dose of 125 mg/m$^2$, 135 mg/m$^2$, 145 mg/m$^2$, e.g., infused over about 2, 3, or 4 hours, or 155 mg/m$^2$, 165 mg/m$^2$, 175 mg/m$^2$, 185 mg/m$^2$, 195 mg/m$^2$, e.g., infused over about 22, 23, 24 or 25 hours, on a schedule. In one embodiment, the schedule is administration of paclitaxel every three weeks. The treatment can further include administration of one or more additional chemotherapeutic agent.

Pyrimidine Analogues

The pharmaceutical composition described herein can be administered in combination with a pyrimidine analogue (e.g., fluorouracil) to treat a subject having cancer, e.g., a primary tumor, or having or at risk of having metastasis of a primary tumor. The administration of pyrimidine analogues such as fluorouracil can be associated with mobilization of bone marrow derived progenitor cells such as endothelial progenitor cells in subjects having cancer.

In one embodiment, the pyrimidine analogue (e.g., fluorouracil) is administered in an amount and/or dosing schedule that is associated with (e.g., causes) bone marrow derived progenitor cell mobilization. For example, the vascular disrupting agent is administered in an amount and/or dosing schedule that is associated with (e.g., causes) endothelial progenitor cell mobilization.

In one embodiment, the cancer is breast cancer (e.g., locally advanced or metastatic breast cancer). The breast cancer can be estrogen receptor positive breast cancer; estrogen receptor negative breast cancer; HER-2 positive breast cancer; HER-2 negative breast cancer; progesterone receptor positive breast cancer; progesterone receptor negative breast cancer; estrogen receptor negative, HER-2 negative and progesterone receptor negative breast cancer (i.e., triple negative breast cancer). The breast cancer can be resistant, relapsed or refractory to treatment with a chemotherapeutic agent, e.g., an alkylating agent (e.g., cyclophosphamide, dacarbazine, melphalan, ifosfamide, temozolomide), an anthracycline (e.g., daunorubicin, doxorubicin, epirubicin, valrubicin and idarubicin), or a taxane (e.g., docetaxel or paclitaxel) or a platinum based agent (e.g. cisplatin). In some embodiments, a pharmaceutical composition described herein can be administered in combination with fluorouracil, e.g., fluorouracil at a dose of 8 mg/m$^2$, 10 mg/m$^2$, 12 mg/m$^2$, 14 mg/m$^2$, 16 mg/m$^2$ on a schedule. In one embodiment, the schedule is administration of fluorouracil once daily for four days, and then, e.g., at a reduced dose on day 6, 8, 10 and 12. The treatment can further include administration of one or more additional chemotherapeutic agent, e.g., an alkylating agent (e.g., cyclophosphamide, dacarbazine, melphalan, ifosfamide, temozolomide), an anthracycline (e.g., daunorubicin, doxorubicin, epirubicin, valrubicin and idarubicin), or a taxane (e.g., docetaxel or paclitaxel). The treatment can further include administration of leucovorin.

In one embodiment, the cancer is colorectal cancer (e.g., locally advanced or metastatic colorectal cancer). The breast cancer can be resistant, relapsed or refractory to treatment with a chemotherapeutic agent. In some embodiments, a pharmaceutical composition described herein can be administered in combination with fluorouracil, e.g., fluorouracil at a dose of 8 mg/m$^2$, 10 mg/m$^2$, 12 mg/m$^2$, 14 mg/m$^2$, 16 mg/m$^2$ on a schedule. In one embodiment, the schedule is administration of fluorouracil once daily for four days, and then, e.g., at a reduced dose on day 6, 8, 10 and 12. The treatment can further include administration of one or more additional chemotherapeutic agent, e.g., an alkylating agent (e.g., cyclophosphamide, dacarbazine, melphalan, ifosfamide, temozolomide), an anthracycline (e.g., daunorubicin, doxorubicin, epirubicin, valrubicin and idarubicin), or a taxane (e.g., docetaxel or paclitaxel). The treatment can further include administration of leucovorin.

In one embodiment, the cancer is gastric cancer (e.g., locally advanced or metastatic gastric cancer). The gastric cancer can be resistant, relapsed or refractory to treatment with a chemotherapeutic agent. In some embodiments, a pharmaceutical composition described herein can be administered in combination with fluorouracil, e.g., fluorouracil at a dose of 8 mg/m$^2$, 10 mg/m$^2$, 12 mg/m$^2$, 14 mg/m$^2$, 16 mg/m$^2$ on a schedule. In one embodiment, the schedule is administration of fluorouracil once daily for four days, and then, e.g., at a reduced dose on day 6, 8, 10 and 12. The treatment can further include administration of one or more additional chemotherapeutic agent, e.g., a platinum based agent (e.g., cisplatin, carboplatin, oxaliplatin), a taxane (docetaxel, paclitaxel) and an anthracycline (e.g., daunorubicin, doxorubicin, epirubicin, valrubicin and idarubicin). The treatment can further include administration of leucovorin.

In one embodiment, the cancer is pancreatic cancer (e.g., locally advanced or metastatic pancreatic cancer). The pancreatic cancer can be resistant, relapsed or refractory to treatment with a chemotherapeutic agent. In some embodiments, a pharmaceutical composition described herein can be administered in combination with fluorouracil, e.g., fluorouracil at a dose of 8 mg/m$^2$, 10 mg/m$^2$, 12 mg/m$^2$, 14 mg/m$^2$, 16 mg/m$^2$ on a schedule. In one embodiment, the schedule is administration of fluorouracil once daily for four days, and then, e.g., at a reduced dose on day 6, 8, 10 and 12. The treatment can further include administration of one or more additional chemotherapeutic agent. The treatment can further include administration of leucovorin.

Growth Factors for Myeloid Cells and Red Blood Cells

The pharmaceutical composition described herein can be administered in combination with a chemotherapeutic agent that is administered in combination with growth factors for blood cells (e.g. myeloid cells, granulocytes, and red blood cells) to treat a subject having cancer, e.g., a primary tumor, or having or at risk of having metastasis of a primary tumor. The administration of a chemotherapeutic agent that requires co administration of a growth factor for blood cells (e.g. myeloid cells and red blood cells), e.g., to counter one or more side effect of the chemotherapeutic agent, may be associated with mobilization of bone marrow derived progenitor cells such as endothelial progenitor cells in subjects having cancer.

In one embodiment, the method includes administering the chemotherapeutic agent in combination with a growth factor and then subsequent administration of a pharmaceutical composition described herein. For example, the pharmaceutical composition can be administered one, two, three, five, ten, fifteen, twenty hours, or 1, 2, 3, 4 days after the administration of the growth factor.

Exemplary growth factors include, but are not limited to, colony stimulating factors (e.g., granulocyte colony stimulating factor (GCSF), granulocyte macrophage colony stimulating factor (GM-CSF)), CXCR4 antagonists, erythropoietin.

In one embodiment, the subject has one of the following cancers: lung cancer (e.g., small cell lung cancer or non small cell lung cancer), urothelial cancer, a nonmyeloid malignancy, breast cancer, ovarian cancer and a neuroblastoma.

In one embodiment, the subject has lung cancer (e.g., small cell lung cancer or non small cell lung cancer) and the method includes administering an anthracycline (e.g., doxorubicin, daunorubicin, epirubicin, idarubicin, mitoxantrone, valrubicin), a topoisomerase inhibitor (e.g., topotecan, irinotecan, etoposide, teniposide, lamellarin D, SN-38, camptothecin) and/or an alkylating agent (e.g., cyclophosphamide, dacarbazine, melphalan, ifosfamide, temozolomide) in combination with an inflammatory growth factor (e.g., a colony stimulating factor, e.g., GCSF, GM-CSF), and then subsequently administering a pharmaceutical composition described herein.

In one embodiment, the subject has urothelial cancer and the method includes administering an anthracycline (e.g., doxorubicin, daunorubicin, epirubicin, idarubicin, mitoxantrone, valrubicin), a topoisomerase inhibitor (e.g., topotecan, irinotecan, etoposide, teniposide, lamellarin D, SN-38, camptothecin) and/or an alkylating agent (e.g., cyclophosphamide, dacarbazine, melphalan, ifosfamide, temozolomide) in combination with a growth factor (e.g., a colony stimulating factor, e.g., GCSF, GM-CSF), in combination with a pharmaceutical composition described herein, e.g., concomitantly or serially.

In one embodiment, the subject has a nonmyeloid cancer and the method includes administering an anthracycline (e.g., doxorubicin, daunorubicin, epirubicin, idarubicin, mitoxantrone, valrubicin), a platinum based agent (e.g., cisplatin, carboplatin, oxaliplatin), a vinca alkaloid (e.g., vinblastine, vincristine, vindesine and vinorelbine) and/or an antimetabolite (e.g., methotrexate) in combination with an inflammatory growth factor (e.g., a colony stimulating factor, e.g., GCSF, GM-CSF), in combination with a pharmaceutical composition described herein, e.g., concomitantly or serially.

In one embodiment, the subject has breast cancer or ovarian cancer and the method includes administering a platinum based agent (e.g., cisplatin, carboplatin, oxaliplatin), a topoisomerase inhibitor (e.g., topotecan, irinotecan, etoposide, teniposide, lamellarin D, SN-38, camptothecin) and/or an alkylating agent (e.g., cyclophosphamide, dacarbazine, melphalan, ifosfamide, temozolomide) in combination with an inflammatory growth factor (e.g., a colony stimulating factor, e.g., GCSF, GM-CSF), in combination with a pharmaceutical composition described herein, e.g., concomitantly or serially.

In one embodiment, the subject has a neuroblastoma and the method includes administering an anthracycline (e.g., doxorubicin, daunorubicin, epirubicin, idarubicin, mitoxantrone, valrubicin), a platinum based agent (e.g., cisplatin, carboplatin, oxaliplatin) and/or an alkylating agent (e.g., cyclophosphamide, dacarbazine, melphalan, ifosfamide, temozolomide) in combination with an inflammatory growth factor (e.g., a colony stimulating factor, e.g., GCSF, GM-CSF), and then subsequently administering a pharmaceutical composition described herein.

Radiation

The pharmaceutical composition described herein can be administered in combination with radiation therapy or surgery to treat a subject having cancer, e.g., a primary tumor, or having or at risk of having metastasis of a primary tumor. As discussed herein, administration of surgery and/or radiation to a subject having cancer is associated with mobilization of bone marrow derived progenitor cells such as EPCs.

Kits

Also within the scope of the disclosure are a kit comprising a pharmaceutical composition described herein, e.g., a pharmaceutical composition described herein that lacks substantial anticoagulation activity; a kit comprising a pharmaceutical composition described herein, e.g., a pharmaceutical composition that includes a LMWH preparation that lacks substantial anticoagulation activity, and instructions to administer the pharmaceutical composition to a subject with cancer who has been or will be treated with a chemotherapeutic agent; a kit comprising a pharmaceutical composition described herein, e.g., a pharmaceutical composition that includes a LMWH preparation that lacks substantial anticoagulation activity, and instructions to administer the composition to a subject with cancer who has been or will be treated with a chemotherapeutic agent at a dose or dosing schedule that is associated with bone marrow derived progenitor cell mobilization.

The kit can include one or more other elements including: other reagents, e.g., a therapeutic agent; devices or other materials for preparing the pharmaceutical composition for administration; pharmaceutically acceptable carriers; and devices or other materials for administration to a subject. The instructions can include instructions for therapeutic application including suggested dosages and/or modes of administration, e.g., in a patient having a disorder, e.g., a disorder described herein. The kit can further contain at least one additional reagent, such as a diagnostic or therapeutic agent, e.g., a diagnostic or therapeutic agent as described herein, formulated as appropriate, in one or more separate pharmaceutical compositions.

OTHER EMBODIMENTS

This invention is further illustrated by the following examples that should not be construed as limiting. The contents of all references, patents and published patent applications cited throughout this application are incorporated herein by reference.

EXAMPLES

Example 1

Unformulated M402

150 mg/mL M402, a low molecular weight heparin described above, was dissolved in sterile water, i.e., in the absence of buffers or excipients, in sealed sterile glass vials. Glass vials were incubated under exemplary accelerating storage conditions, which in this Example included room temperature at ambient relative humidity for predetermined time periods illustrative of long term storage conditions expected for commercially marketed M402. Multiple attributes of the drug were then assessed.

Attribute assessment revealed increased levels of formic acid, as detected by 1D-NMR methods disclosed herein, and increased levels of $C_2H_6O_3$, as detected by 2D-NMR methods. These data support that formulations could be used to improve M402 stability.

Example 2

Formulated M402|Various Formulations|Time-Point Zero

Formulations of M402 were prepared to assess M402 stability. All formulations were prepared using 'water for injection' (WFI) and the agents shown in Table 1. Formulation pH was adjusted to within +/−0.1 pH units of the value shown in Table 1 using HCl or NaOH as appropriate and formulations were filtered through a 0.2 µm filter. 1.5 mL of each formulation was then dispensed into sealed glass vials with a final concentration of M402 of 150 mg/mL. In some instances, Nitrogen (N2) was used to assess the impact of headspace gas on M402 stability. The N2 overlay was prepared as follows: Empty glass vials were placed in a box with an N2 environment (99.99% purity N2), air was purged from the vials with N2, and then samples were prepared and added to vials. More specifically, a glove box was purged with N2 gas, maintaining positive pressure and less than 10% relative humidity (RH). For each formulation, empty vials were placed in the glove box. Using a secondary N2 source with tubing, N2 was dispensed into each vial to displace air by holding the tubing over each vial for 4-5 seconds. 1.5 mL of each solution was then dispensed into the vial before capping and sealing with a stopper and crimp cap. In other instances, ascorbic acid was added at a final concentration of 1% (v/v). Attributes of the formulations were assessed at zero days.

Attributes assessed included: appearance and color (criteria required was clear, colorless to slightly yellow solution)—performed weekly, pH, percent M402 in solution, osmolality, percent impurities, and M402 weight average molecular weight (mW). pH was assessed using standard methods known in the art and standard equipment, namely a Fisher Scientific Accumet Research AR25 Dual Channel pH/Ion Meter (Catalog # 13-636-AR25B) with a Mettler Toledo, Type: InLab Micro, Model: 51343160 probe. Osmolality was measured using freezing point depression per USP<785> and the instrument used was the Advanced Instruments Model 3250 with a 290 mOsmol/kg standard. Percent impurities were assessed using the 1D-NMR method to detect formic acid and the 2D-NMR method to detect $C_2H_6O_3$ disclosed herein. M402 molecular weight was assessed using the method disclosed herein. M402 in solution was assessed via HPLC and reported as percent relative to M402 control (i.e., a prior sample of a M402 that passed required quality checks and that is stored dry until use as a control run contemporaneously with test sample). TABLE 1 shows data for assessed attributes.

TABLE 1

| Formulation M402 (150 mg/mL) + | pH | M402 in Solution (%) | Osmo (mOsm/L) | Impurities (%) | mW (Daltons) |
|---|---|---|---|---|---|
| 30 mM sodium citrate | 6.1 | 93 | 430 | 0.1 | 6649 |
| 30 mM sodium citrate + N2 overlay | 6.0 | 93 | 433 | 0.2 | 6658 |
| 30 mM sodium citrate + Ascorbic acid | 6.1 | 93 | 530 | 0.3 | 6497 |
| 10 mM sodium citrate | 6.0 | 95 | 373 | 0.1 | 6670 |
| 30 mM Histidine | 7.4 | 94 | 371 | 0.1 | 6633 |
| 30 mM Histidine + N2 overlay | 7.5 | 94 | 374 | 0.1 | 6669 |
| 30 mM Histidine + Ascorbic acid | 6.9 | 93 | 476 | 4.2 | 6454 |
| 10 mM Histidine | 7.3 | 94 | 353 | 0.1 | 6608 |
| 30 mM maleate | 6.8 | 92 | 417 | 0.2 | 6647 |
| 10 mM maleate | 6.6 | 93 | 365 | 0.2 | 6660 |

TABLE 1-continued

| Formulation M402 (150 mg/mL) + | pH | M402 in Solution (%) | Osmo (mOsm/L) | Impurities (%) | mW (Daltons) |
|---|---|---|---|---|---|
| 30 mM sodium phosphate | 7.5 | 94 | 407 | 0.4 | 6664 |
| 10 mM sodium phosphate | 7.3 | 95 | 362 | 0.3 | 6662 |

Data shown in Table 1 supports that M402 can be formulated in various buffers and that formulation may impact certain attributes of M402 at the time of formulation. Of note, multiple buffer and pH combinations were successfully formulated without significant change in either the amount of impurities or the molecular weight. Although the initial profile of M402 in solution is important, the degradation rate of M402 is also informative for assessment of various M402 formulations.

Example 2. TABLE 2 shows data for several assessed attributes, including pH, percent impurities, and M402 weight average molecular weight (mW).

TABLE 2

| Formulation M402 (150 mg/mL) + | 2-weeks | | | 4-weeks | | | 8-weeks | | |
|---|---|---|---|---|---|---|---|---|---|
| | pH | Impurities (%) | mW (Da) | pH | Impurities (%) | mW (Da) | pH | Impurities (%) | mW (Da) |
| 30 mM sodium citrate | 6.0 | 0.3 | 6675 | 6.0 | 0.7 | 6654 | 6.0 | 0.9 | 6713 |
| 30 mM sodium citrate + N2 | 6.0 | 0.3 | 6664 | 6.0 | 0.7 | 6594 | 6.0 | 1.1 | 6730 |
| 30 mM sodium citrate + Asc | 5.8 | 7 | 6152 | 5.8 | 6.2 | 6072 | 5.7 | 8.9 | 5890 |
| 10 mM sodium citrate | 5.9 | 0.5 | 6663 | 6.0 | 0.6 | 6697 | 5.9 | 1.1 | 6669 |
| 30 mM Histidine | 7.3 | 2 | 6526 | 7.2 | 4.4 | 6471 | 7.1 | 11.8 | 6470 |
| 30 mM Histidine + N2 | 7.4 | 1.4 | 6571 | 7.3 | 3.3 | 6445 | 7.2 | 7.1 | 6374 |
| 30 mM Histidine + Asc | 6.5 | 23.2 | 6260 | 6.5 | 22.8 | 6276 | 6.5 | 29.3 | 6151 |
| 10 mM Histidine | 7.1 | 0.7 | 6610 | 7.0 | 1.3 | 6633 | 6.8 | 6.2 | 6599 |
| 30 mM maleate | 6.8 | 0.3 | 6647 | 6.8 | 0.7 | 6651 | 6.7 | 1.1 | 6664 |
| 10 mM maleate | 6.5 | 0.2 | 6643 | 6.5 | 0.8 | 6564 | 6.4 | 0.9 | 6700 |
| 30 mM sodium phosphate | 7.4 | 0.5 | 6561 | 7.4 | 1.4 | 6592 | 7.3 | 1.7 | 6462 |
| 10 mM sodium phosphate | 7.3 | 0.5 | 6586 | 7.2 | 1.0 | 6724 | 7.1 | 1.1 | 6497 |

Example 3

Formulated M402|Various Formulations|Accelerating Conditions 1

M402 was formulated as described in Example 2 and glass vials were incubated under accelerating storage conditions, at 25° C. at 60% relative humidity. These conditions were selected to accelerate any degradation of M402. Attributes of the formulations were assessed at 2-week, 4-week, and 8-week time points. Attributes assessed included pH, percent M402 in solution, formulation osmolality, percent impurities, and M402 weight average molecular weight (mW). Methods for attribute assessment are as provided in Data shown in TABLE 2, and TABLE 1, demonstrate that formulation impacts certain attributes of M402 at 25° C. at 60% relative humidity. For example, the data show that certain attributes of M402 alter at 25° C. at 60% relative humidity, suggesting breakdown of M402, and that certain formulations protect M402 from such change. For example, with the exception of '30 mM sodium citrate+Asc' and all histidine formulations, the percent impurities did not increase more than 2%. In contrast, the osmolality for '30 mM sodium citrate+Asc' and 'all histidine formulations increased by greater than 6% (19 units for '30 mM sodium citrate+Asc' and 11 units for '30 mM histidine+Asc'). Additionally, percent M402 in solution remained moderately stable at each time point with the largest decrease (4%) observed for 10 mM histidine. 30 mM sodium citrate alone or with N2 or Asc, showed the lowest decrease in percent M402 in solution (0%, +1%, and +2% respectively).

Example 4

Formulated M402|Various Formulations|Accelerating Conditions 2

M402 was formulated as described in Example 2 and glass vials were incubated at accelerating storage conditions, 50° C. at ambient relative humidity. Attributes of the formulations were assessed at 2-week, 4-week, and 8-week time points. Attributes assessed included pH, percent M402 in solution, osmolality, percent impurities, and M402 weight average molecular weight (mW). Methods for attribute assessment are as provided in Example 2. TABLE 3 shows data for several assessed attributes, including pH, percent impurities, and M402 weight average molecular weight (mW).

TABLE 3

| Formulation | 2-weeks | | | 4-weeks | | | 8-weeks | | |
|---|---|---|---|---|---|---|---|---|---|
| M402 (150 mg/mL) + | pH | Impurities (%) | mW (Da) | pH | Impurities (%) | mW (Da) | pH | Impurities (%) | mW (Da) |
| 30 mM sodium citrate | 5.9 | 3.8 | 5676 | 5.6 | 10.1 | 4518 | 5.3 | 22.2 | 3577 |
| 30 mM sodium citrate + N2 | 6.0 | 3.5 | 5783 | 5.9 | 6.8 | 4880 | 5.8 | 15.4 | 4147 |
| 30 mM sodium citrate + Asc | 5.9 | 4.6 | 4990 | 6.2 | 11 | 4403 | 6.6 | 20.9 | 3981 |
| 10 mM sodium citrate | 5.8 | 2.7 | 5546 | 5.3 | 11.9 | 4239 | 5.0 | 26 | 3353 |
| 30 mM Histidine | 6.7 | 26.7 | 5685 | 5.9 | 24.3 | 4670 | 5.4 | 36 | 3617 |
| 30 mM Histidine + N2 | 7.1 | 11.1 | 5658 | 6.8 | 16.9 | 5548 | 6.3 | 27.5 | 4715 |
| 30 mM Histidine + Asc | 6.6 | 28.5 | 518 | 6.4 | 35.2 | 4665 | 6.3 | 47.5 | 3928 |
| 10 mM Histidine | 5.7 | 13.9 | 5342 | 5.1 | 22.7 | 3637 | 4.9 | 33 | 3183 |
| 30 mM maleate | 6.5 | 3.7 | 5901 | 6.2 | 5 | 4957 | 5.8 | 13 | 4230 |
| 10 mM maleate | 6.1 | 4.1 | 5756 | 5.5 | 9 | 4431 | 5.2 | 23.8 | 3393 |
| 30 mM sodium phosphate | 7.0 | 3.6 | 5866 | 6.7 | 4.1 | 5321 | 6.3 | 10.2 | 4700 |
| 10 mM sodium phosphate | 6.6 | 3.6 | 5853 | 5.9 | 8 | 4933 | 5.3 | 20.7 | 3641 |

Data shown in TABLE 3, and TABLE 1, demonstrate that formulation impacts certain attributes of M402 at 50° C. at ambient relative humidity. For example, the data show that certain attributes of M402 alter at 50° C. at ambient relative humidity. Furthermore, the changes shown in TABLE 3 are more pronounced than those shown in TABLE 2, suggesting more substantial breakdown of M402 at 50° C. at ambient relative humidity than at 25° C. at 60% relative humidity, as shown in TABLE 2. However, data in TABLE 3 support that certain formulations protect M402 at 50° C. at ambient relative humidity. Data in Table 3 and Table 1 demonstrate that M402 is more stable, as measured by % impurities, at the upper end of the pH range evaluated (e.g., at pH 6-5-7.5). Data also support that use of anaerobic conditions in the headspace, such a use of N2 (rather than air) as headspace gas, improve M402 stability even in lower pH conditions (see, e.g., M402+citrate).

What is claimed is:

1. A pharmaceutical composition comprising a low molecular weight heparin (LMWH) preparation, wherein the LMWH preparation has the following characteristics:
   (a) a weight average chain molecular weight between 3,500 and 8,000 Da;
   (b) anti-Xa activity of less than 20 IU/mg and anti-IIa activity of 20 IU/mg or less;
   (c) greater than 5% and less than 50% glycol split uronic acid residue (Ug) in the preparation; and one or more buffering agents selected from the group consisting of a citrate buffer, a phosphate buffer, a maleate buffer, and a combination thereof, wherein when stored at a pH of about 6.0 to about 7.5, 25° C. and 60% relative humidity, for a duration of from 2 weeks to 8 weeks, impurities selected from the group consisting of formic acid and $C_2H_6O_3$ are detectable in the composition, but at less than 2%, as determined by the combination of 1D-NMR for formic acid and 2D-NMR for $C_2H_6O_3$.

2. The pharmaceutical composition of claim 1, wherein the LMWH preparation has a molecular weight distribution such that 10-40% of the oligosaccharides of the preparation have a molecular weight <3000 Da; 45-65% of the oligosaccharides have a molecular weight between 3000-8000 Da; and 15-30% of the oligosaccharides have a molecular weight >8000 Da, hereafter an M402 preparation.

3. The pharmaceutical composition of claim 1, wherein the LMWH preparation has a molecular weight distribution such that 10-50% of the oligosaccharides of the preparation have a molecular weight <3000 Da; 40-65% of the oligosaccharides have a molecular weight between 3000-8000 Da, and 5-30% of the oligosaccharides have a molecular weight >8000 Da.

4. The pharmaceutical composition of claim 1, wherein the LMWH preparation has an anti-IIa activity of 1 IU/mg or less.

5. The pharmaceutical composition of claim 1, wherein the pharmaceutical composition contains 150 mg mL$^{-1}$ of the LMWH preparation.

6. The pharmaceutical composition of claim 1, further comprising one or more alcohols.

7. The pharmaceutical composition of claim 1, further comprising one or more antioxidants.

8. The pharmaceutical composition of claim 1, wherein the buffering agent is a citrate buffer.

9. The pharmaceutical composition of claim 8, wherein the concentration of the citrate buffer is 5 to 40 mM.

10. The pharmaceutical composition of claim 8, further comprising an antioxidant.

11. The pharmaceutical composition of claim 8, wherein the citrate buffer is sodium citrate.

12. The pharmaceutical composition of claim 11, wherein the concentration of the citrate buffer is 10-30 mM.

13. The pharmaceutical composition of claim 11, wherein the citrate buffer is 10 mM.

14. The pharmaceutical composition of claim 11, wherein the pH of the composition is 6.0-7.0.

15. The pharmaceutical composition of claim 11, wherein the pH of the composition is 6.5.

16. The pharmaceutical composition of claim 8, wherein the concentration of the citrate buffer is 10-30 mM.

17. The pharmaceutical composition of claim 8, wherein the concentration of the citrate buffer is 10 mM.

18. The pharmaceutical composition of claim 8, wherein the pH of the composition is 6.0-7.0.

19. The pharmaceutical composition of claim 8, wherein the pH of the composition is 6.5.

20. A container comprising the pharmaceutical composition of claim 8, comprising an anaerobic overlay.

21. A container comprising the pharmaceutical composition of claim 1.

22. A method comprising administering the pharmaceutical composition of claim 1 to a subject in need thereof.

23. A method of treating a subject having a disorder, comprising administering to a subject in need thereof the pharmaceutical composition of claim 1.

24. The method of claim 23, wherein the disorder is cancer.

25. The method of claim 24, wherein the cancer is pancreatic cancer.

26. A method of manufacturing an M402 preparation, according to claim 2, the method comprising: obtaining a first polysaccharide preparation comprising unfractionated heparin; depolymerizing the first polysaccharide preparation for a time and under conditions to obtain a second polysaccharide preparation having a weight average molecular weight of 3-8 kDa; modifying the second polysaccharide preparation to obtain a third polysaccharide preparation comprising at least one chain having a glycol split uronic acid residue, and formulating the third polysaccharide preparation with one more of the buffering agents; to thereby manufacture the M402 preparation.

27. A method of manufacturing an M402 preparation according to claim 2, the method comprising: (a) obtaining a preparation of unfractionated heparin (UFH); (b) depolymerizing the UFH for a time and under conditions to obtain a first low molecular weight heparin (LMWH) preparation having a weight average molecular weight of 3000-8000 Da; (c) glycol splitting the first LMWH preparation to obtain a second LMWH preparation; (d) reducing and purifying the second LMWH preparation to obtain a third polysaccharide preparation comprising at least one chain having a glycol split uronic acid residue; (e) formulating the third LMWH preparation with one or more of the buffering agents; to thereby manufacture the M402 preparation.

* * * * *